United States Patent
Ferrera et al.

(10) Patent No.: US 7,326,225 B2
(45) Date of Patent: *Feb. 5, 2008

(54) VASOOCCLUSIVE DEVICE FOR TREATMENT OF ANEURYSMS

(75) Inventors: David A. Ferrera, Manhattan Beach, CA (US); Daniel R. Kurz, Sunnyvale, CA (US); Lok A. Lei, San Jose, CA (US); Julia A. Larsen, San Mateo, CA (US)

(73) Assignee: Micrus Endovascular Corporation, San Jose, CA (US)

(*) Notice: Subject to any disclaimer, the term of this patent is extended or adjusted under 35 U.S.C. 154(b) by 659 days.

This patent is subject to a terminal disclaimer.

(21) Appl. No.: 10/628,767

(22) Filed: Jul. 28, 2003
(Under 37 CFR 1.47)

(65) Prior Publication Data
US 2004/0243168 A1 Dec. 2, 2004

Related U.S. Application Data

(63) Continuation of application No. 09/762,539, filed as application No. PCT/US98/25822 on Dec. 4, 1998, now Pat. No. 6,616,617, which is a continuation-in-part of application No. 09/019,841, filed on Feb. 6, 1998, now Pat. No. 6,159,165, which is a continuation-in-part of application No. 08/986,004, filed on Dec. 5, 1997, now abandoned.

(51) Int. Cl.
*A61M 29/00* (2006.01)
*A61B 17/08* (2006.01)

(52) U.S. Cl. ............... 606/200; 606/157; 606/158; 606/213

(58) Field of Classification Search ............ 606/151, 606/191–200, 157, 213; 600/585; 128/898
See application file for complete search history.

(56) References Cited

U.S. PATENT DOCUMENTS 1,341,052 A 5/1920 Gale (Continued)

FOREIGN PATENT DOCUMENTS

DE 41 02 550 A1 8/1991

(Continued)

OTHER PUBLICATIONS

English Language Summary of JP 8-280814 reference.

(Continued)

*Primary Examiner*—Glenn K. Dawson
*Assistant Examiner*—Kathleen Sonnett
(74) *Attorney, Agent, or Firm*—Fulwider Patton LLP

(57) ABSTRACT

The device is formed from a multi-stranded micro-cable having a plurality of flexible strands of a shape memory material and at least one radiopaque strand. The strands can be made of a shape memory nickel titanium alloy, that is highly flexible at a temperature appropriate for introduction into the body via a catheter, and that after placement will take on the therapeutic shape. The radiopaque strand can have a core strand with a plurality of intermittently spaced apart enlarged radiopaque portions that may be a plurality of beads of radiopaque material spaced apart and mounted on the core strand, or a plurality of coils intermittently wound about and spaced apart on the core strand. A polyhedral occlusive device is also provided, adapted to be inserted into a portion of a vasculature for occluding a portion of the vasculature, for use in interventional therapy and vascular surgery.

18 Claims, 12 Drawing Sheets

U.S. PATENT DOCUMENTS

| | | | |
|---|---|---|---|
| 1,667,730 A | 5/1928 | Green | |
| 2,078,182 A | 4/1937 | MacFarland | |
| 2,549,335 A | 4/1951 | Rahthus | |
| 3,334,629 A | 8/1967 | Cohn | |
| 3,452,745 A | 7/1969 | Muller | |
| 3,485,234 A | 12/1969 | Stevens | |
| 3,649,224 A | 3/1972 | Anderson | |
| 3,868,956 A | 3/1975 | Alfidi et al. | |
| 4,161,952 A | 7/1979 | Kinney et al. | |
| 4,205,680 A | 6/1980 | Marshall | |
| 4,257,421 A | 3/1981 | Beal | |
| 4,494,531 A | 1/1985 | Gianturco | |
| 4,500,658 A | 2/1985 | Fox | |
| 4,502,482 A | 3/1985 | DeLuccia et al. | |
| 4,512,338 A | 4/1985 | Balko et al. | |
| 4,553,545 A | 11/1985 | Maass et al. | |
| 4,580,568 A | 4/1986 | Gianturco | |
| 4,629,458 A | 12/1986 | Pinchuk | |
| 4,638,803 A | 1/1987 | Rand | |
| 4,655,771 A | 4/1987 | Wallsten | |
| 4,670,286 A | 6/1987 | Nyilas et al. | |
| 4,682,607 A | 7/1987 | Vaillancourt et al. | |
| 4,718,907 A | 1/1988 | Karwoski et al. | |
| 4,748,986 A | 6/1988 | Morrison et al. | |
| 4,768,507 A | 9/1988 | Fischell et al. | |
| 4,795,458 A | 1/1989 | Regan | |
| 4,795,741 A | 1/1989 | Leshchiner et al. | |
| 4,798,606 A | 1/1989 | Pinchuk | |
| 4,800,882 A | 1/1989 | Gianturco | |
| 4,813,925 A | 3/1989 | Anderson, Jr. et al. | |
| 4,820,298 A | 4/1989 | Leveen et al. | |
| 4,830,003 A | 5/1989 | Wolff et al. | |
| 4,832,055 A | 5/1989 | Palestrant | |
| 4,850,960 A | 7/1989 | Grayzel | |
| 4,856,516 A | 8/1989 | Hillstead | |
| 4,922,924 A | 5/1990 | Gambale et al. | |
| 4,932,419 A | 6/1990 | de Toledo | |
| 4,950,258 A | 8/1990 | Kawai et al. | |
| 4,954,126 A | 9/1990 | Wallsten | |
| 4,957,479 A | 9/1990 | Roemer | |
| 4,957,501 A | 9/1990 | Lahille et al. | |
| 4,990,155 A | 2/1991 | Wilkoff | |
| 4,994,069 A * | 2/1991 | Ritchart et al. | 606/191 |
| 4,998,916 A | 3/1991 | Hammerslag et al. | |
| 5,019,090 A | 5/1991 | Pinchuk | |
| 5,025,799 A | 6/1991 | Wilson | |
| 5,026,377 A | 6/1991 | Burton et al. | |
| 5,037,377 A | 8/1991 | Alonso | |
| 5,037,391 A | 8/1991 | Hammerslag et al. | |
| 5,041,084 A | 8/1991 | DeVries et al. | |
| 5,055,101 A | 10/1991 | McCoy | |
| 5,061,275 A | 10/1991 | Wallstén et al. | |
| 5,063,935 A | 11/1991 | Gambale | |
| 5,064,435 A | 11/1991 | Porter | |
| 5,065,769 A | 11/1991 | de Toledo | |
| 5,071,407 A | 12/1991 | Termin et al. | |
| 5,092,847 A | 3/1992 | Pozzo | |
| 5,104,404 A | 4/1992 | Wolff | |
| 5,108,407 A | 4/1992 | Geremia et al. | |
| 5,111,829 A | 5/1992 | Alvarez de Toledo | |
| 5,122,136 A | 6/1992 | Guglielmi et al. | |
| 5,129,890 A | 7/1992 | Bates et al. | |
| 5,133,731 A | 7/1992 | Butler et al. | |
| 5,133,732 A | 7/1992 | Wiktor | |
| 5,135,516 A | 8/1992 | Sahatjian et al. | |
| 5,139,243 A | 8/1992 | Balsells | |
| 5,141,502 A | 8/1992 | Macaluso, Jr. | |
| 5,143,085 A | 9/1992 | Wilson | |
| 5,147,370 A | 9/1992 | McNamara et al. | |
| 5,151,105 A | 9/1992 | Kwan-Gett | |
| 5,152,784 A | 10/1992 | Tsilibary | |
| 5,160,341 A | 11/1992 | Brenneman et al. | |
| 5,167,233 A | 12/1992 | Eberle et al. | |
| 5,171,273 A | 12/1992 | Silver et al. | |
| 5,174,302 A | 12/1992 | Palmer | |
| 5,176,625 A | 1/1993 | Brisson | |
| 5,176,661 A | 1/1993 | Evard et al. | |
| 5,183,085 A | 2/1993 | Timmermans | |
| 5,184,627 A | 2/1993 | de Toledo | |
| 5,186,992 A | 2/1993 | Kite, III | |
| 5,197,977 A | 3/1993 | Hoffman, Jr. et al. | |
| 5,203,772 A | 4/1993 | Hammerslag et al. | |
| 5,211,183 A | 5/1993 | Wilson | |
| 5,211,658 A | 5/1993 | Clouse | |
| 5,213,111 A | 5/1993 | Cook et al. | |
| 5,217,484 A | 6/1993 | Marks | |
| 5,222,969 A | 6/1993 | Gillis | |
| 5,226,911 A | 7/1993 | Chee et al. | |
| 5,228,453 A | 7/1993 | Sepetka | |
| 5,230,348 A | 7/1993 | Ishibe et al. | |
| 5,234,437 A | 8/1993 | Sepetka | |
| 5,234,456 A | 8/1993 | Silvestrini | |
| 5,238,004 A | 8/1993 | Sahatjian et al. | |
| 5,241,970 A | 9/1993 | Johlin, Jr. et al. | |
| 5,243,996 A | 9/1993 | Hall | |
| 5,246,014 A | 9/1993 | Williams et al. | |
| 5,250,071 A | 10/1993 | Palermo | |
| 5,251,640 A | 10/1993 | Osborne | |
| 5,253,653 A | 10/1993 | Daigle et al. | |
| 5,256,146 A | 10/1993 | Ensminger et al. | |
| 5,258,042 A | 11/1993 | Mehta | |
| 5,259,393 A | 11/1993 | Corso, Jr. et al. | |
| 5,303,714 A | 4/1994 | Abele et al. | |
| 5,304,121 A | 4/1994 | Sahatjian | |
| 5,304,194 A | 4/1994 | Chee et al. | |
| 5,312,415 A | 5/1994 | Palermo | |
| 5,336,205 A | 8/1994 | Zenzen et al. | |
| 5,341,818 A | 8/1994 | Abrams et al. | |
| 5,342,387 A | 8/1994 | Summers | |
| 5,350,397 A | 9/1994 | Palermo et al. | |
| 5,354,295 A | 10/1994 | Guglielmi et al. | |
| 5,356,388 A | 10/1994 | Sepetka et al. | |
| 5,368,049 A | 11/1994 | Raman et al. | |
| 5,373,856 A | 12/1994 | Grenouillet | |
| 5,382,259 A * | 1/1995 | Phelps et al. | 606/151 |
| 5,386,828 A | 2/1995 | Owens et al. | |
| 5,409,015 A | 4/1995 | Palermo | |
| 5,413,597 A | 5/1995 | Krajicek | |
| 5,417,708 A | 5/1995 | Hall et al. | |
| 5,421,338 A | 6/1995 | Crowley et al. | |
| 5,423,829 A | 6/1995 | Pham et al. | |
| 5,423,849 A * | 6/1995 | Engelson et al. | 606/191 |
| 5,429,597 A | 7/1995 | DeMello et al. | |
| 5,437,282 A | 8/1995 | Koger et al. | |
| 5,439,485 A | 8/1995 | Mar et al. | |
| 5,441,516 A | 8/1995 | Wang et al. | |
| 5,443,478 A | 8/1995 | Purdy | |
| 5,460,187 A | 10/1995 | Daigle et al. | |
| 5,462,523 A | 10/1995 | Samson et al. | |
| 5,465,732 A | 11/1995 | Abele | |
| 5,486,193 A | 1/1996 | Bourne et al. | |
| 5,514,115 A | 5/1996 | Frantzen et al. | |
| 5,514,128 A | 5/1996 | Hillsman et al. | |
| 5,514,176 A | 5/1996 | Bosley, Jr. | |
| 5,520,194 A | 5/1996 | Miyata et al. | |
| 5,522,819 A | 6/1996 | Graves et al. | |
| 5,522,822 A | 6/1996 | Phelps et al. | |
| 5,522,836 A | 6/1996 | Palermo | |
| 5,523,092 A | 6/1996 | Hanson et al. | |
| 5,527,338 A | 6/1996 | Purdy | |
| 5,527,354 A | 6/1996 | Fontaine et al. | |
| 5,531,715 A | 7/1996 | Engelson et al. | |
| 5,540,680 A | 7/1996 | Guglielmi et al. | |
| 5,540,701 A | 7/1996 | Sharkey et al. | |

| | | | |
|---|---|---|---|
| 5,540,713 A | 7/1996 | Schnepp-Pesch et al. | |
| 5,549,624 A * | 8/1996 | Mirigian et al. | 600/191 |
| 5,549,663 A | 8/1996 | Cottone, Jr. | |
| 5,562,641 A | 10/1996 | Flomenblit et al. | |
| 5,562,698 A | 10/1996 | Parker | |
| 5,569,245 A | 10/1996 | Guglielmi et al. | |
| 5,582,619 A | 12/1996 | Ken | |
| 5,601,593 A | 2/1997 | Freitag | |
| 5,603,694 A | 2/1997 | Brown et al. | |
| 5,607,445 A | 3/1997 | Summers | |
| 5,609,627 A | 3/1997 | Goicoechea et al. | |
| 5,618,301 A | 4/1997 | Hauenstein et al. | |
| 5,624,449 A | 4/1997 | Pham et al. | |
| 5,624,461 A | 4/1997 | Mariant | |
| 5,632,772 A | 5/1997 | Alcime et al. | |
| 5,637,113 A | 6/1997 | Tartaglia et al. | |
| 5,639,277 A | 6/1997 | Mariant et al. | |
| 5,643,254 A | 7/1997 | Scheldrup et al. | |
| 5,645,082 A | 7/1997 | Sung et al. | |
| 5,645,558 A | 7/1997 | Horton | |
| 5,649,949 A | 7/1997 | Wallace et al. | |
| 5,658,308 A * | 8/1997 | Snyder | 606/191 |
| 5,667,522 A | 9/1997 | Flomenblit et al. | |
| 5,669,931 A | 9/1997 | Kupiecki et al. | |
| 5,669,933 A | 9/1997 | Simon et al. | |
| 5,676,697 A | 10/1997 | McDonald | |
| 5,683,411 A | 11/1997 | Kavteladze et al. | |
| 5,690,643 A | 11/1997 | Wijay | |
| 5,690,666 A | 11/1997 | Berenstein et al. | |
| 5,690,667 A | 11/1997 | Gia | |
| 5,690,671 A | 11/1997 | McGurk et al. | |
| 5,693,085 A | 12/1997 | Buirge et al. | |
| 5,700,258 A * | 12/1997 | Mirigian et al. | 606/1 |
| 5,709,707 A | 1/1998 | Lock et al. | |
| 5,718,711 A | 2/1998 | Berenstein et al. | |
| 5,720,764 A | 2/1998 | Naderlinger | |
| 5,725,572 A | 3/1998 | Lam et al. | |
| 5,733,294 A | 3/1998 | Forber et al. | |
| 5,733,326 A | 3/1998 | Tomonto et al. | |
| 5,733,329 A | 3/1998 | Wallace et al. | |
| 5,741,327 A | 4/1998 | Frantzen | |
| 5,749,891 A | 5/1998 | Ken et al. | |
| 5,749,894 A | 5/1998 | Engelson | |
| 5,762,615 A | 6/1998 | Weier | |
| 5,766,219 A | 6/1998 | Horton | |
| 5,782,909 A | 7/1998 | Quiachon et al. | |
| 5,800,511 A | 9/1998 | Mayer | |
| 5,800,525 A | 9/1998 | Bachinski et al. | |
| 5,814,062 A | 9/1998 | Sepetka et al. | |
| 5,814,064 A | 9/1998 | Daniel et al. | |
| 5,817,100 A | 10/1998 | Igaki | |
| 5,824,042 A | 10/1998 | Lombardi et al. | |
| 5,824,045 A | 10/1998 | Alt | |
| 5,824,071 A | 10/1998 | Nelson et al. | |
| 5,824,077 A | 10/1998 | Mayer | |
| 5,843,118 A | 12/1998 | Sepetka et al. | |
| 5,876,432 A * | 3/1999 | Lau et al. | 623/1.13 |
| 6,013,084 A * | 1/2000 | Ken et al. | 606/108 |
| 6,093,199 A * | 7/2000 | Brown et al. | 606/200 |
| 6,136,015 A * | 10/2000 | Kurz et al. | 606/191 |
| 6,159,165 A * | 12/2000 | Ferrera et al. | 600/585 |
| 6,168,592 B1 * | 1/2001 | Kupiecki et al. | 606/32 |
| 6,171,326 B1 * | 1/2001 | Ferrera et al. | 606/191 |
| 6,193,708 B1 * | 2/2001 | Ken et al. | 606/1 |
| 6,287,331 B1 * | 9/2001 | Heath | 623/1.15 |
| 6,306,153 B1 * | 10/2001 | Kurz et al. | 606/191 |
| 6,340,367 B1 * | 1/2002 | Stinson et al. | 623/1.34 |
| 6,399,886 B1 * | 6/2002 | Avellanet | 174/128.1 |
| 6,616,617 B1 * | 9/2003 | Ferrera et al. | 600/585 |
| 2007/0016233 A1 * | 1/2007 | Ferrera et al. | 606/159 |

FOREIGN PATENT DOCUMENTS

| | | |
|---|---|---|
| DE | 197 04 269 A1 | 11/1997 |
| EP | 0 183 372 A1 | 6/1986 |
| EP | 0 278 937 A2 | 8/1988 |
| EP | 0 382 014 A1 | 8/1990 |
| EP | 0 518 704 AI | 12/1992 |
| EP | 0 627 201 A1 | 12/1994 |
| EP | 0 743 047 A3 | 11/1996 |
| EP | 0 747 014 A1 | 12/1996 |
| EP | 0 778 005 A1 | 6/1997 |
| EP | 0 820 726 A2 | 1/1998 |
| FR | 592.182 | 5/1925 |
| GB | 2 066 839 A | 7/1981 |
| JP | 6-218063 | 8/1994 |
| JP | 2505772 | 5/1996 |
| JP | 8-280814 | 10/1996 |
| WO | 92/14408 | 9/1992 |
| WO | 94/09705 | 5/1994 |
| WO | 94/10936 | 5/1994 |
| WO | 94/16619 | 8/1994 |
| WO | 94/16629 | 8/1994 |
| WO | 95/18585 | 7/1995 |
| WO | 95/21592 | 8/1995 |
| WO | 96/32907 | 10/1996 |
| WO | WO 97/19643 | 6/1997 |
| WO | 97/26939 | 7/1997 |
| WO | 97/31672 | 9/1997 |
| WO | 97/48351 | 12/1997 |
| WO | 99/05977 | 2/1999 |
| WO | 99/07294 | 2/1999 |

OTHER PUBLICATIONS

English Language Summary of JP 2505772 reference.

Christos A. Athanasoulis, M.D., The New England Journal of Medicine, May 15, 1980, "Therapeutic Applications of Angiography" pp. 1117-1125.

Christos A. Athanasoulis, M.D., The New England Journal of Medicine, May 22, 1980, "Therapeutic Applications of Angiography" pp. 1174-1179.

Alex Berenstein, M.D. and Irvin I. Kricheff, M.D., "Catheter and Material Selection for Transarterial Embolization: Technical Considerations" Radiology, Sep. 1979; pp. 631-639.

O.A. Battista, et al. Journal of Applied Polymer Science 1967 "Colloidal Macromolecular Phenomena. Part II. Novel Microcrystals of Polymers" pp. 481-498.

Sadek K. Hilal, M.D. et al. Journal of Neurological Surgery "Therapeutic Percutaneous Embolization for Extra-Axial Vascular Lesions of the Head, Neck, and Spine" Sep. 1975; pp. 275-287.

Stephen L. Kaufman, M.D. et al. Investigate Radiology, May-Jun. 1978, "Transcatheter Embolization With Microfibrillar Collagen in Swine"; pp. 200-204.

Ashok J. Kumar, et al., Journal of Neuroradiology (1982) "Preoperative Embolization of Hypervascular Head and Neck Neoplasms Using Microfibrillar Collagen", pp. 163-168.

Richard E. Latchaw, M.D. et al., Radiology (1979) "Polyvinyl Foam Embolization of Vascular and Neoplastic Lesions of the Head, Neck and Spine" pp. 669-679.

Stewart R. Reuter, M.D. et al. American Journal of Radiology, Sep. 1975, "Selective Arterial Embolization for Control of Massive Upper Gastrointestinal Bleeding" pp. 119-126.

Glenn H. Roberson, et al., American Journal of Radiology, Oct. 1979, "Therapeutic Embolization of Juvenile Angiofibroma" pp. 657-663.

Sidney Wallace, M.D. et al., Cancer, Oct. 1979, "Arterial Occlusion of Pelvic Bone Tumors"; pp. 322-325 & 661-663.

C. Gianturco, M.D., et al., "Mechanical Devices for Arterial Occlusion", Jul. 1975, pp. 428-435.

"Therapeutic Vascular Occlusion Utilizing Steel Coil Technique: Clinical Applications" by Sidney Wallace, et al., Am J. Roentgenol (1976); pp. 381-387.

"Transcatheter Intravascular Coil Occlusion of Experimental Arteriovenous Fistulas", by James H. Anderson, et al., Am. J. Roentgenol, Nov. 1977, pp. 795-798.

"'Mini' Ginaturco Stainless Steel Coils for Transcatheter Vascular Occlusion" by James H. Anderson, et al., From the Department of Diagnostic Radiology at the University of Texas Cancer Center, Aug. 1978, pp. 301-303.

"A New Improved Coil for Tapered-Tip Catheter for Arterial Occlusion" by Vincent P. Chuang, M.D., et al., May 1980, pp. 507-509.

"Neurosurgery Interactive Article Part 2—Clinical Studies Embolization of Cerebral Arteriovenous Malformations: Part II—Aspects of Complications and Late Outcome" by Christer Lunqvist, M.D., PH.D., et al., Sep. 96, pp. 1-16.

"Shape Memory Alloys" by Jeff Perkins, pp. 1095-1096.

Y. Pierre Gobin, M.D., et al., "Treatment of Large and Giant Fusiform Intracranial Aneurysms With Guglielmi Detachable Coils", J. Neurosurg., Jan. 1996, pp. 55-62, vol. 84.

Cameron G. McDougall, M.D., et al., "Endovascular Treatment of Basilar Tip Aneurysms Using Electrolytically Detachable Coils", J. Neurosurg., Mar. 1996, pp. 393-399, vol. 84.

Scott C. Standard, M.D., et al., "Retrieval of Guglielmi Detachable Coil After Unraveling and Fracture: Case Report and Experimental Results", Neurosurgery, Nov. 1994, pp. 994-999, vol. 35, No. 5.

Gary Duckwiler, M.D., et al., "Catheters, Embolic Agents Spark Neurointervention", Diagnostic Imaging, May 1994, pp. 66-70 & 102.

Retrievable Gianturco-Coil Introducer, by Jeffrey Hawkins, Ronald G. Quisling, MD, J. Parker Mickel, MD and Irvin F. Hawkins, MD (Radiology 1986) From the Depts. of Radiology and Neurosurgery, University of Florida Medical Center and Hawk Prototype Equipment, Gainesville, FL.

* cited by examiner

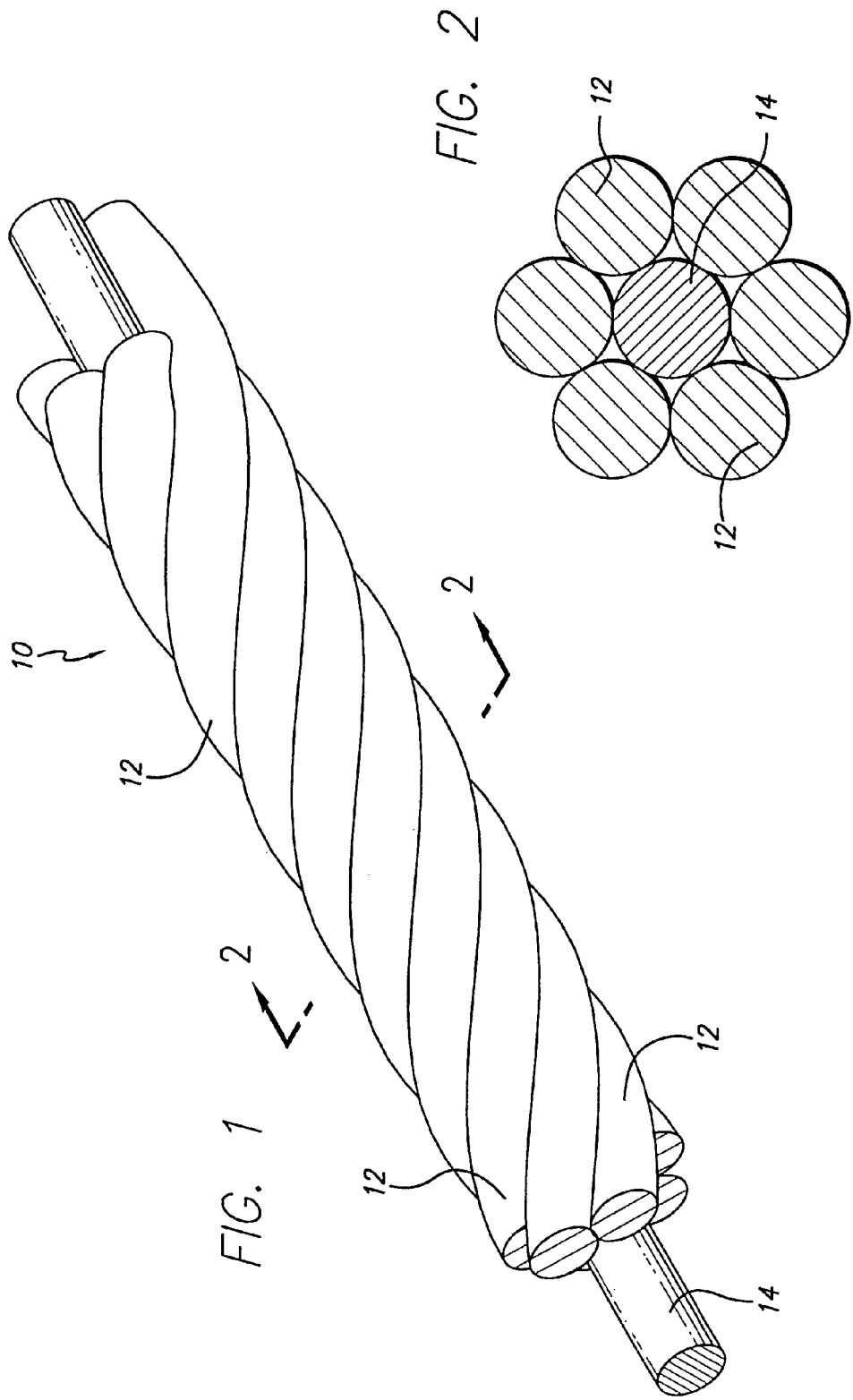

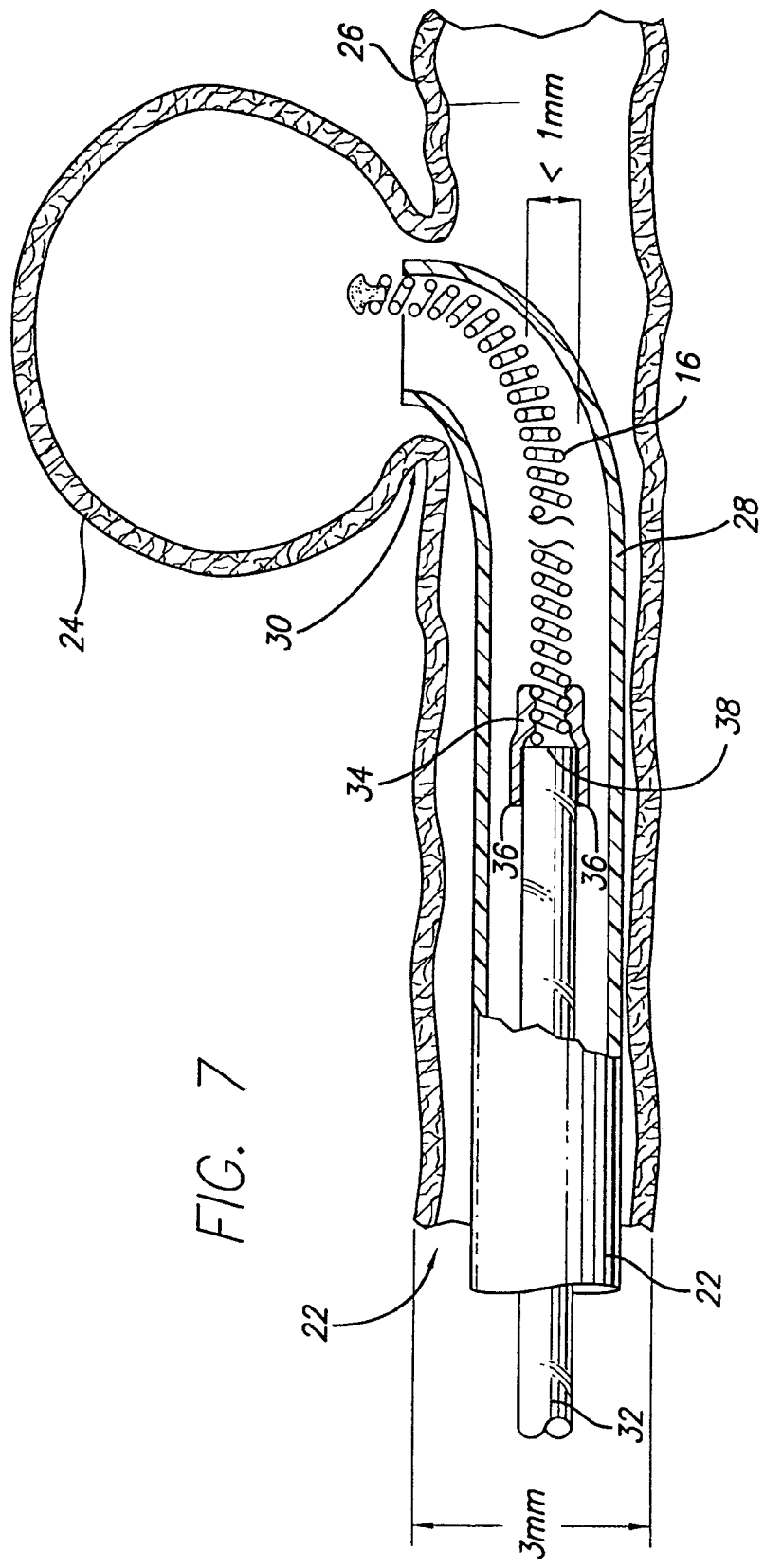

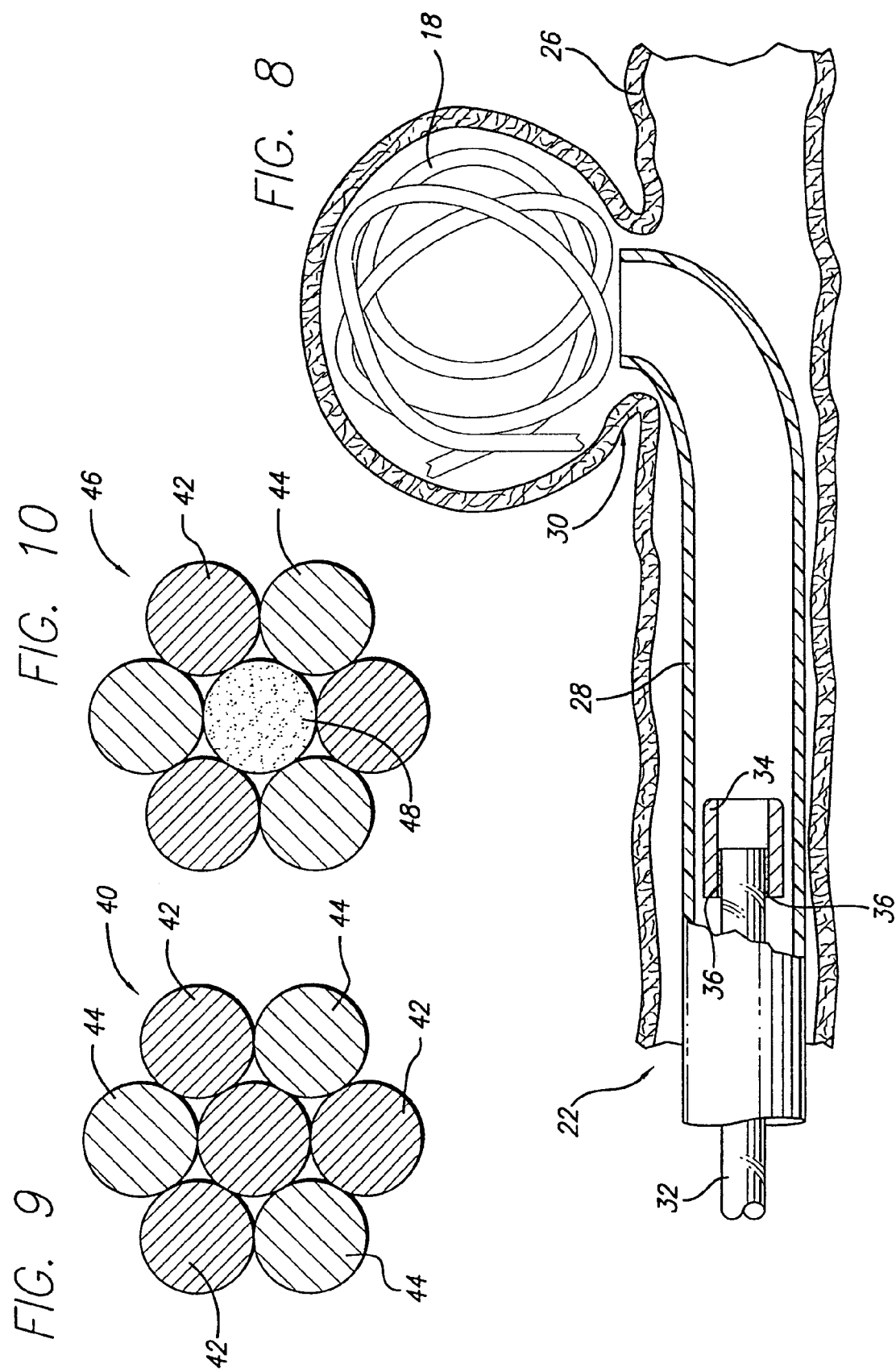

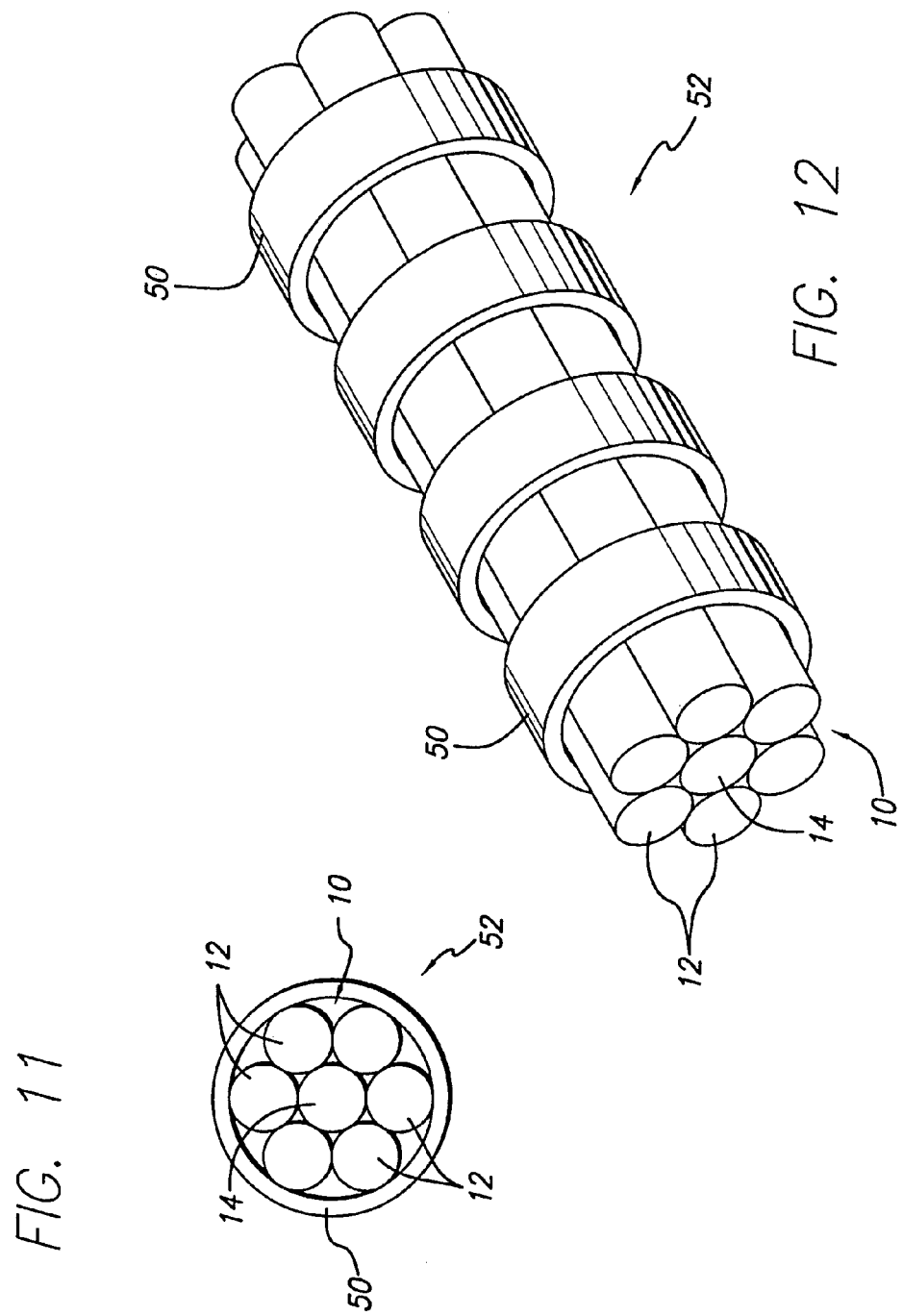

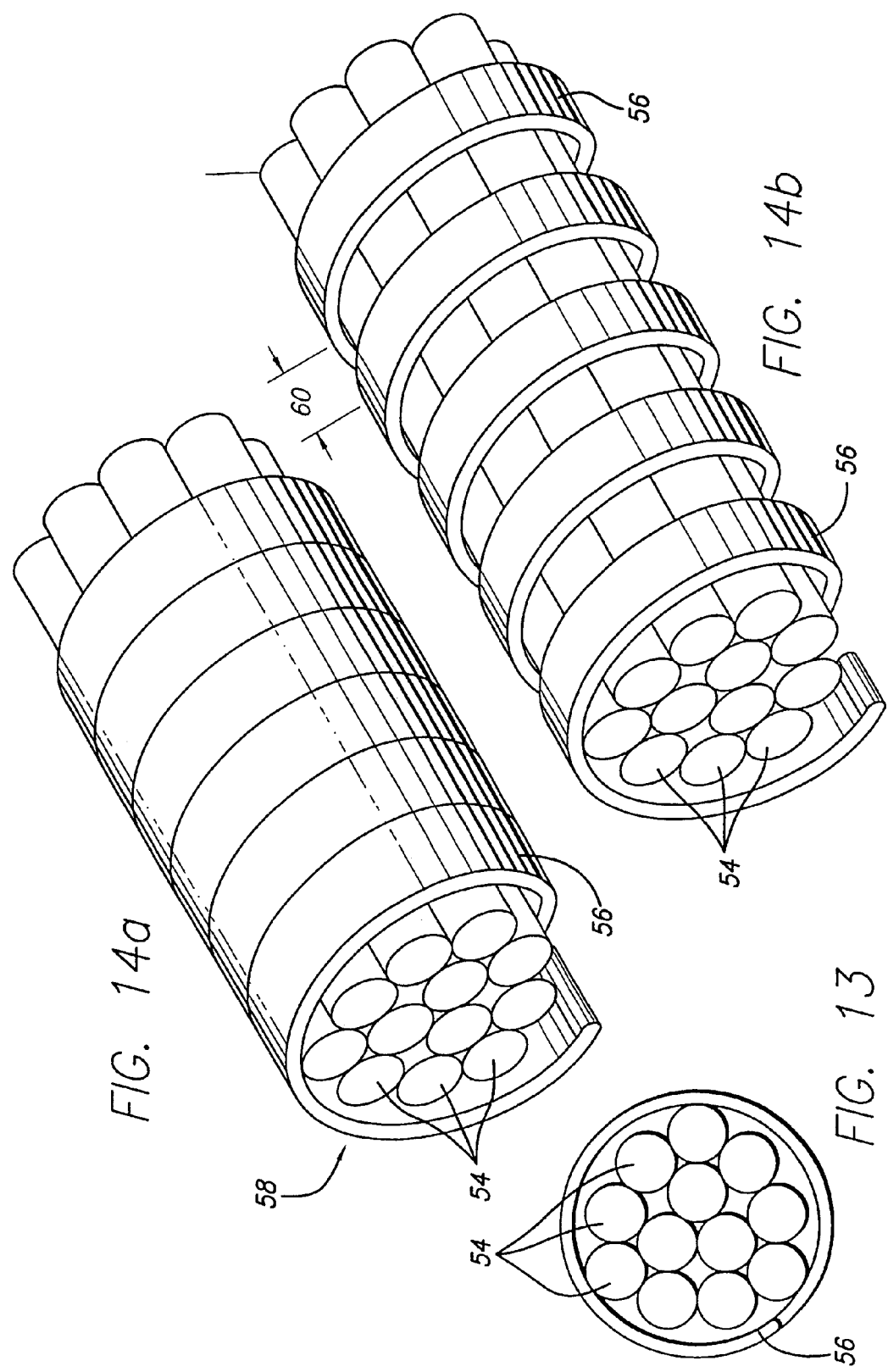

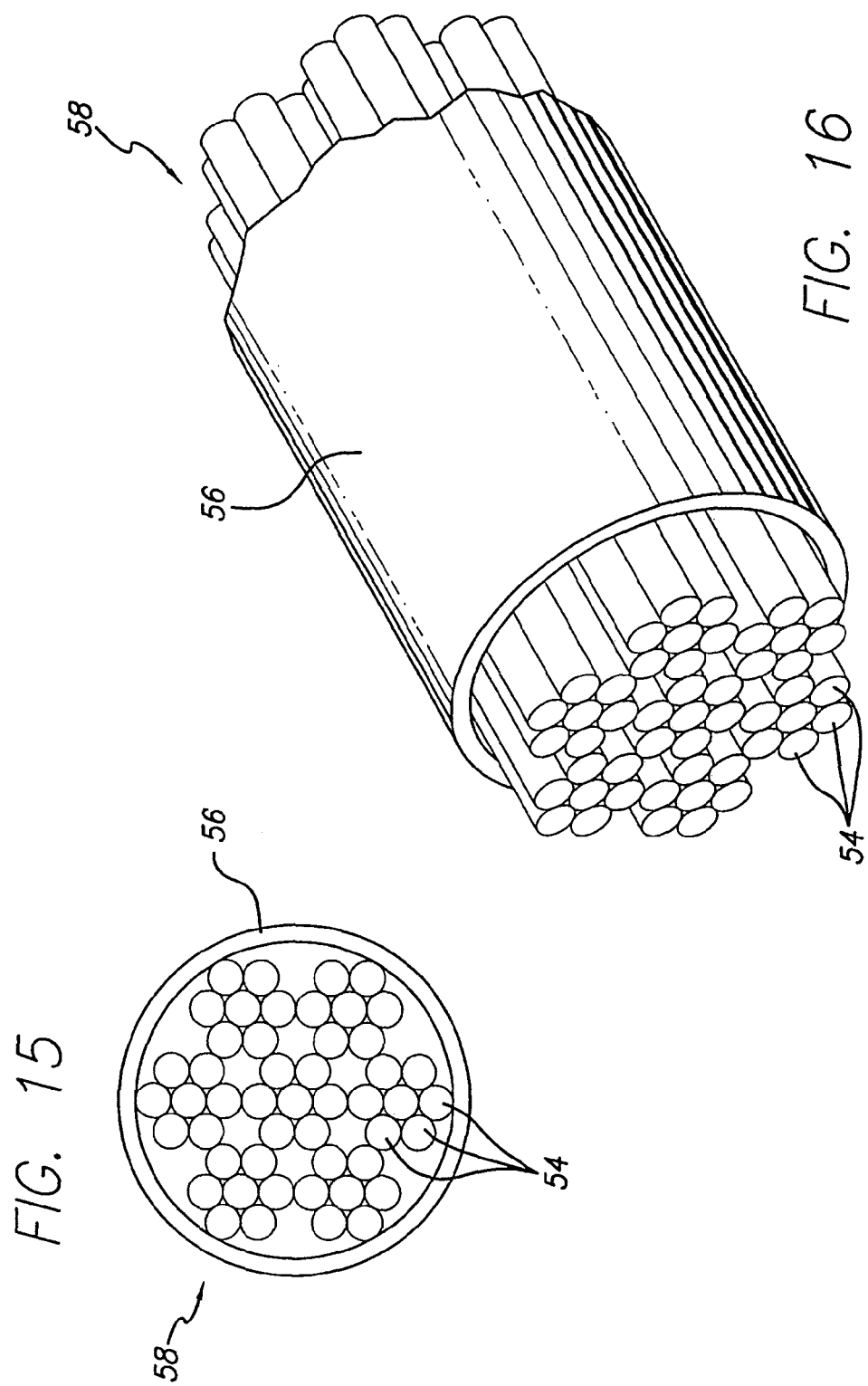

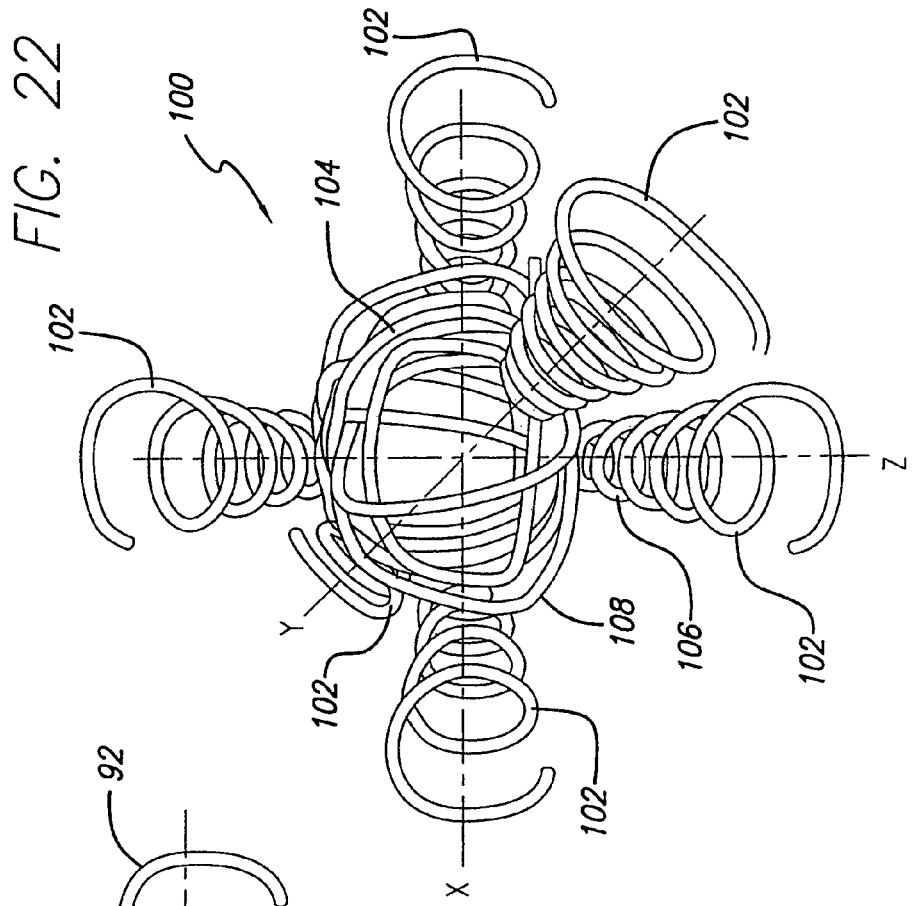
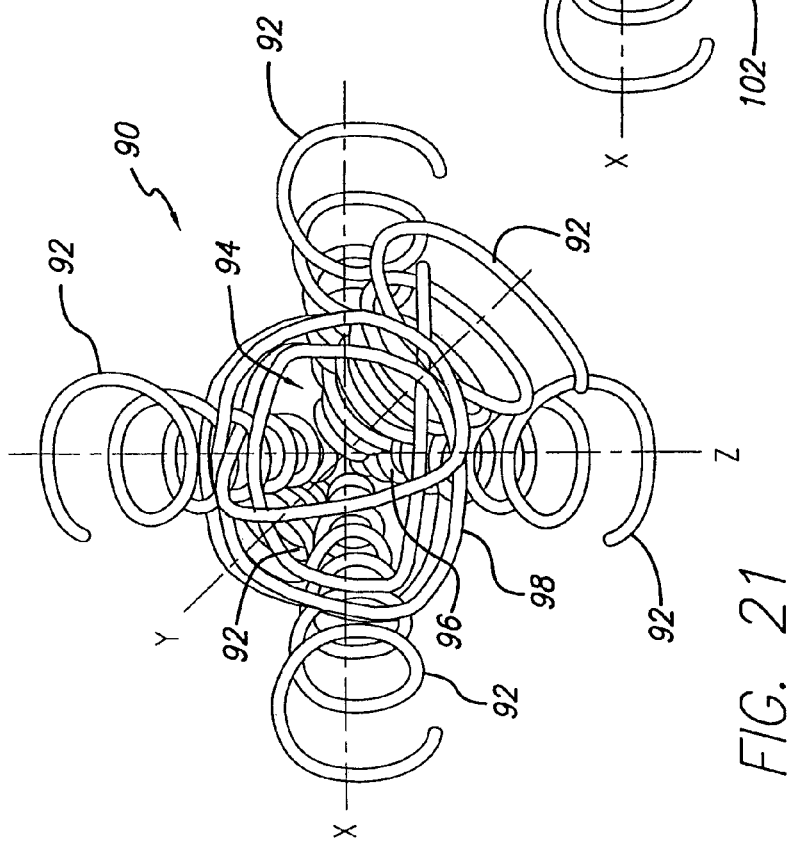

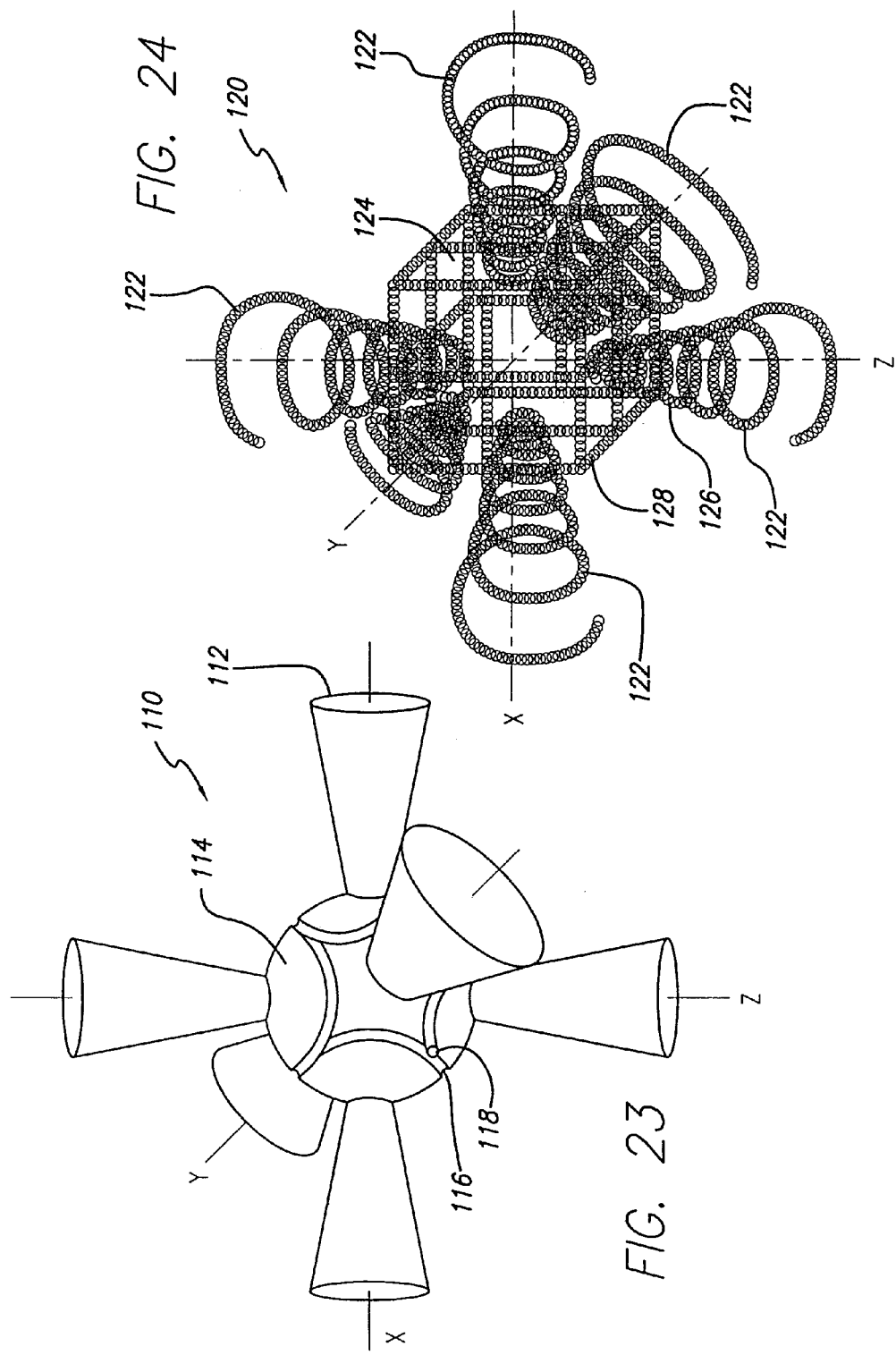

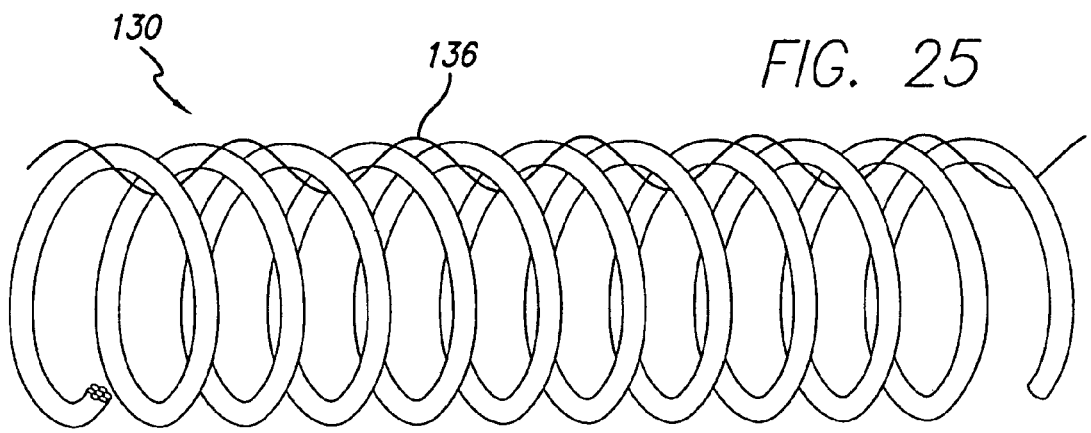
FIG. 25
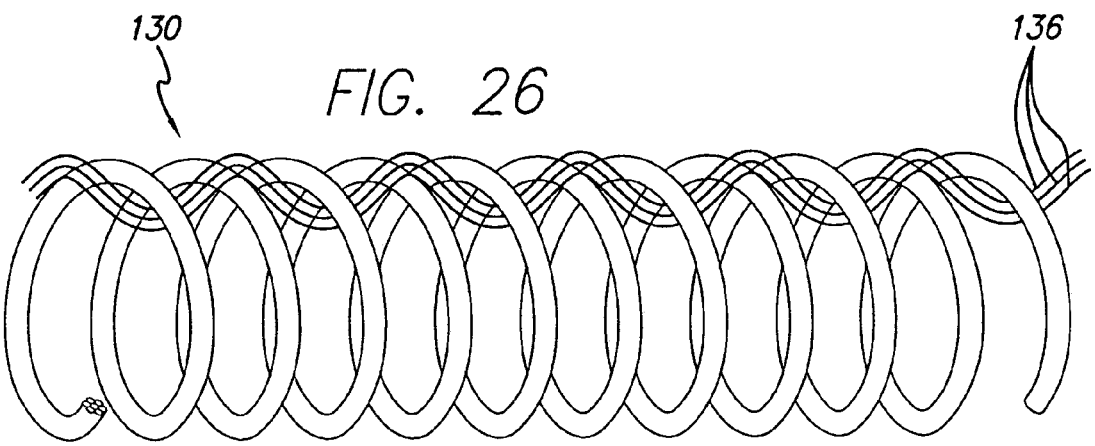
FIG. 26
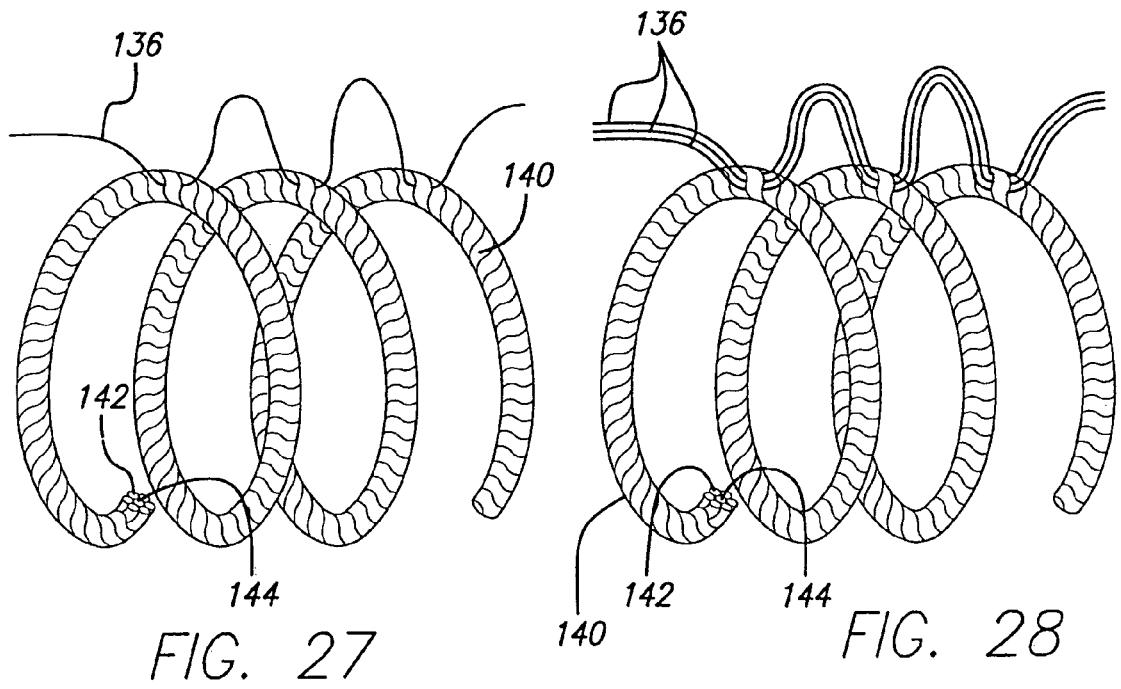
FIG. 27
FIG. 28

VASOOCCLUSIVE DEVICE FOR TREATMENT OF ANEURYSMS

RELATED APPLICATIONS

This is a Continuation of Ser. No. 09/762,539 filed Feb. 8, 2001, now U.S. Pat. No. 6,616,617, which is a 371 of International PCT/US98/25822 filed Dec. 4, 1998, which is a continuation-in-part of Ser. No. 09/019,841 filed Feb. 6, 1998 now U.S. Pat. No. 6,159,165, which was a continuation-in-part of Ser. No. 08/986,004 filed Dec. 5, 1997 now abandoned.

BACKGROUND OF THE INVENTION

1. Field of the Invention

This invention relates generally to implantable devices for interventional therapeutic treatment or vascular surgery, and concerns a stranded micro-cable with enhanced radiopacity that can be used to fabricate a vascular device, a stent, a guidewire or the like. More particularly, the invention relates to three dimensional microcoil vasoocclusive devices fabricated from stranded micro-cable.

2. Description of Related Art

The art and science of interventional therapy and surgery has continually progressed towards treatment of internal defects and diseases by use of ever smaller incisions or access through the vasculature or body openings, in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

One specific field of interventional therapy that has been able to advantageously use recent developments in technology is the treatment of neurovascular defects. More specifically, as smaller and more capable structures and materials have been developed, treatment of vascular defects in the human brain which were previously untreatable or represented unacceptable risks via conventional surgery have become amenable to treatment. One type of non-surgical therapy that has become advantageous for the treatment of defects in the neurovasculature has been the placement by way of a catheter of vasoocclusive devices in a damaged portion of a vein or artery.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645,558, which is specifically incorporated by reference herein. That vasoocclusive device comprises one or more vasoocclusive members wound to form a generally spherical or ovoid shape in a relaxed state. The vasoocclusive members can be a helically wound coil or a co-woven braid formed of a biocompatible material, and the device is sized and shaped to fit within a vascular cavity or vesicle, such as for treatment of an aneurysm or fistula. The vasoocclusive member can be first helically wound or braided in a generally linear fashion, and is then wound around an appropriately shaped mandrel or form, and heat treated to retain the shape after removal from the heating form. Radiopacity can be provided in the vasoocclusive members by weaving in synthetic or natural fibers filled with powdered radiopaque material, such as powdered tantalum, powdered tungsten, powdered bismuth oxide or powdered barium sulfate, which can potentially be released during vascular surgery.

Another occlusion device for closing defects in vascular walls is known that is formed by a pair of distinct sections of varying configuration, which may be parabolic or conical bodies oriented to flare outward. Yet another implantable vasoocclusive device is known that is formed by a complex, helically wound coil adapted to take on a secondary shape suitable for snugly fitting within a given vascular cavity upon deployment, that can be formed by winding the coil on a mandrel having radially extending poles.

The delivery of such vasoocclusive devices can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro coils, in that they can have super-elastic or shape memory properties, and thus can be manufactured to easily fit into a linear portion of a catheter, but attain their originally formed, more complex shape when deployed. Although various materials are more or less kink resistant when nickel-titanium alloys are dimensioned into wire smaller than approximately 0.010 inches in diameter, they can have low yield strength and can kink more easily, thus severely limiting the applications for such finely drawn wire in the fabrication of vasoocclusive devices. As a further limitation to such applications, nickel-titanium alloys are also not radiopaque in small diameters, and a single nickel-titanium wire would need to be approximately 0.012 inches in diameter to be even slightly radiopaque. However, such a thickness of a single nickel-titanium wire would unfortunately also be relatively stiff and possibly traumatic to the placement site, particularly if used for treatment of delicate and already damaged areas of the small diameter vasculature such as an aneurysm in an artery or vein in the brain, for example.

One conventional guidewire for use in a catheter is known that is made of a high elasticity nickel-titanium alloy, and is useful for accessing peripheral or soft tissue targets. The distal tip of the guidewire is provided with a radiopaque flexible coil tip, and a radiopaque end cap is attached to the guidewire by a radiopaque ribbon. Such a construction is complex to manufacture, fragile and can potentially break off during use with undesirable results. A stretch resistant vasoocclusive coil is also known that can be made of a primary helically wound coil of platinum wire, with a stretch-resisting wire attached within the primary coil between two end caps. Unfortunately, such a construction is relatively difficult to fabricate and also fragile, allowing for the possibility of the fracture of the central radiopaque wire, the coil, the welds or some combination of them, and it can also potentially break off during use. Also, such a construction has a complex and nonlinear bending characteristic, dependent on the spacing of the coils and central wire and the radius of the bend of the coil.

From the above, it can be seen that vasoocclusive devices and their attendant deployment systems provide important improvements in the treatment of damaged neurovascular areas. However, there remain important limitations in the technology presently available to fabricate these devices. It would therefore be desirable to provide a structural element that can be incorporated into a stent, guidewire, micro-coil or the like, which offers the advantages of a shape memory alloy such as a nickel-titanium alloy, and that incorporates radiopaque material in a stable configuration that is not subject to breaking during use of the device, so that the device can be visualized under fluoroscopy. It would also be desirable to be able to create a variety of three dimensional vasoocclusive shapes that can be deployed from a catheter into an aneurysm or other defect and to thereby provide an efficient therapy for treatment of the defect. The present invention meets these and other needs.

SUMMARY OF THE INVENTION

Significant advances have been made in the treatment of neurovascular defects without resolution to surgery. More specifically, micro catheters have been developed which allow the placement of vasoocclusive devices in an area of the vasculature which has been damaged. In presently used techniques, the vasoocclusive devices take the form of spiral wound wires that can take more complex three dimensional shapes as they are inserted into the area to be treated. By using materials that are highly flexible, or even super-elastic and relatively small in diameter, the wires can be installed in a micro-catheter in a relatively linear configuration and assume a more complex shape as it is forced from the distal end of the catheter.

In order to gain the advantages presently being realized with micro-catheter therapies and procedures to repair damage to the vasculature in the brain and other vessels, shape memory materials such as nickel-titanium alloys have been incorporated in vasoocclusive devices to be placed by the catheters. However, the range of diameters of wire and the configurations of the resulting geometry of both the coils and the devices developed which can be used have been limited by both the relatively small diameter of wire that must be used to avoid trauma and allow housing within the catheter prior to deployment, and the requirement for larger diameters to provide for radiopaque markers and mechanical robustness. In many cases this has resulted in primary wire characteristics in the coil that are unacceptably stiff, very delicate, or subject to kinking. The present invention obtains significant advantages over such prior art devices by providing a cable of multiple strands of an alloy adapted to be used in catheters, stents, vasoocclusive devices, guidewires and the like, thus providing a kink resistant, high strength material with highly desirable performance characteristics which can be altered by construction details to suit a variety of interventional therapeutic procedures.

More specifically, it has been found that single strands of small diameter nickel-titanium alloys, as well as other metal alloys, used to form vasoocclusive devices can be kinked if twisted and pulled as can occur during or after deployment from a catheter, especially if the doctor wishes to withdraw a partially deployed coil because it is somehow incorrect in size, shape or length to repair the damage to the vessel. Also, single wire coils are more likely to cause trauma to the area to be treated if the wire is of a sufficient diameter to provide adequate tensile strength. Furthermore, such small diameter wires of some of these materials such as nickel-titanium, stainless steel and the like, are not generally radiopaque with currently available equipment, necessitating the use of radiopaque markers attached to the device, with the resultant possible diminution of functionality and increased diameter.

The present invention solves these and other problems by providing, in its broadest aspect, a micro-cable which includes at least one radiopaque strand to offer a continuous indication under fluoroscopy of the deployed configuration of the device incorporating the micro-cable. When combined with the benefits of a material such as nickel-titanium in the other strands of the micro-cable, numerous advantages are available from the use of this basic construction in interventional medicine.

Briefly, and in general terms, a presently preferred embodiment of the present invention provides for a multi-stranded micro-cable made of a suitable material such as stainless steel or a nickel-titanium alloy, with the cable including at least one radiopaque strand, made of platinum, tungsten or gold, in order to serve as a marker during a procedure. The multi-stranded micro-cable can be configured into a stent, guidewire, micro-coil or the like used in micro-catheters, for example, to restrict, reinforce, or to occlude areas of the small diameter vasculature such as an artery or vein in the brain, for example, for treatment of aneurysms and the like.

In one presently preferred embodiment, the invention accordingly provides for a multi-stranded micro-cable formed of a plurality of flexible strands of a super elastic material, and at least one radiopaque strand. In one presently preferred embodiment, the multi-stranded micro-cable comprises a plurality of flexible strands of nickel-titanium alloy, the micro-cable having at least one central axially disposed radiopaque wire, such as platinum, tungsten or gold, for example, in order to provide a radiopaque marker during vascular procedures. In this preferred embodiment, the construction of the invention places the lowest tensile strength and highest flexibility member, the radiopaque marker strand, in a position in the cable which results in minimum stress on that member; at the same time, the super elastic material is in the outer strands, which have the dominant affect on performance parameters, thus enhancing the benefits of the material. Another benefit associated with the invention compared to prior art devices is that the multiple stranded cable configuration, in addition to providing a highly flexible and resilient structure, eliminates the necessity of a safety wire, since the failure of a single strand will not cause a severing of the cable. Also, the construction prevents stretching of the cable in the event of failure of a single strand, which is a significant benefit compared to constructions which have a coil around a central safety wire.

In a second presently preferred embodiment, the invention includes a multi stranded cable constructed of multiple twisted strands of a suitable material such as a shape memory alloy or super-elastic alloy of nickel-titanium, with one or more of the twisted strands consisting of a radiopaque material. The radiopaque strand may be one or more of the peripheral twisted strands and may also include one or more central strands of the cable. In a preferred aspect of the embodiment, the cable consists of six peripheral twisted strands and a central linear core strand, one or more of which can be of radiopaque material.

In a third aspect of the invention, the cable can be of linear strands that are arranged in a bundle and fastened or bound at intervals, or continuously, in order to maintain contact among the strands as the cable is bent. One or more of the strands may be radiopaque. This construction is adaptable to guidewires and other structures that must be pushable and/or torqueable, but still remain highly flexible and include radiopacity. Variations on this embodiment can include an outer sheath which consists of a solid or helically wound cover to provide enhanced torqueability and pushability. More specifically, the outer sheath can vary in thickness, stiffness of material or spring of the sheath members to provide desired variations in bending or stiffness of the cable. Such a construction is particularly adaptable to guidewires and the like, and can be varied in terms of the binding or outer layer to alter the torqueability of the cable, and the flexibility of the cable can be varied along its length by the number and sizes of the stranded members in the cable.

In a fourth aspect of the invention, one or more of the strands can be of a therapeutic material used to enhance treatment of the site after placement of the device. In one presently preferred embodiment of the invention, the cable includes twisted strands of wire around the periphery of the cable, at least one of which is radiopaque. Such a construction can be adapted to a variety of interventional therapeutic treatments, such as providing both a therapeutic effect and also contributing to the structural integrity of the cable. By using copper in such a micro-cable, for instance, the copper can enhance the use of a device made from the cable as an intrauterine device, with the copper also contributing to the radiopacity and structural integrity of the micro-cable. In the event that such an effect is desired, the therapeutic strand can be placed on the exterior of the cable to enhance contact with the site to be treated.

In a fifth aspect of the invention, a three dimensional occlusive device is provided that is adapted to be inserted into a portion of a vasculature for occluding the portion of the vasculature for use in interventional therapy and vasculature surgery, that comprises at least one multi-stranded micro-cable having a plurality of flexible strands of a resilient material, with at least one radiopaque strand to provide a radiopaque marker of the deployed configuration of device made of the cable during vascular surgery. The occlusive device is configured to have a primary, collapsed coil configuration or shape, and an expanded, or secondary three dimensional coil configuration or shape, that can be generally helical, conical, or spherical shapes. The flexible strands in a multi-stranded micro-cable of the occlusive device can be helically wound, or can be configured as parallel, longitudinal strands. In a currently preferred embodiment, at least one of the strands comprises a super-elastic material. In another currently preferred embodiment, a plurality of the strands comprises a super-elastic material. One presently preferred super-elastic material comprises a nickel titanium alloy, that can be heat treated such that the alloy is highly flexible at a temperature appropriate for introduction into the body via a catheter, and after placement, the device will seek its minimum energy shape as originally formed and thereby take on a shape designed to optimize the therapeutic purposes desired for the device.

In another aspect of the invention, at least one of the strands comprises a shape memory material. In another currently preferred embodiment, a plurality of the strands are comprised of a shape memory material. One presently preferred shape memory material comprises a shape memory polymer. In one configuration, the strands of the micro-cable are arranged as exterior strands surrounding at least one interior strand, or core, and at least one radiopaque strand is disposed in the micro-cable, either centrally, axially disposed in the bundle of strands, or in the exterior strands surrounding the central core. The micro-cable can include a plurality of radiopaque strands, such as platinum, gold, or tungsten.

In the fifth aspect of the invention, at least one of the strands in the core or exterior strands can comprise a therapeutic agent, such as a copper or copper alloy wire or any of a variety of therapeutically active metals, alloys or components, a fiber such as Dacron (polyester), polyglycolic acid, polylactic acid, fluoropolymers, nylon, polyaramid fiber (e.g. Kevlar®), or silk chosen for thrombogenicity. Since the micro-cable consists of stranded parts, one or more strands may be longer than others, or even intermittently terminated, to thereby extend beyond the diameter of the remaining strands and thereby increase the therapeutic effect of that strand. Alternatively, at least one of the strands can be coated with or impregnated with a therapeutic material, which can include, but is not limited to, any one or combination of human growth hormone, genetic material, antigens, hydrogels, collagen, bio-absorbable polymers such as lactic acids/glycolic acids, caprolactam or microcellular foam. In addition, the therapeutic element can comprise a means to conduct energy, such as an optical fiber to conduct light energy.

In the fifth aspect of the invention, the strands of the micro-cable can also be bundled by at least one outer cover or sheath to constrain the strands of the micro-cable about a longitudinal axis to produce a composite banded cable. The outer sheath can comprise a containment strand wound about the strands and made of a low friction material, such as a fluoropolymer, for example, or a heat shrinkable plastic tube. In one feature of the fifth aspect of the invention, a plurality of heat shrink plastic covers are placed over the strands of the micro-cable to provide bending stiffness in the cable. The strands of the micro-cable can be banded at intervals by a plurality of bands. In another variation, a plurality of micro-cables that are arranged as parallel, longitudinal micro-cables or a helically wound micro-cables to form a composite cable can have an exterior wrapped cover that can be wound at greater or lesser intervals along the outside to provide variations in the torqueability and stiffness of the composite cable. Also, the thickness and width of the wrapping cover, as well as its material composition along the composite cable can vary in cross section along the length of the composite cable to provide bending stiffness of said cable which varies with the position on said cable. Also, the number of strands and the degree to which they extend along the composite cable can be varied within the sheath, and the outer sheath itself can be multi-layered with different materials in order to provide a graduated bending and stiffness characteristic over the length of the cable. The occlusive device thus can be formed of a plurality of micro-cables in order to provide desired bending and strength characteristics, either as helically wound micro-cables, or parallel longitudinal micro-cables having a collapsed composite cable configuration and an expanded composite cable configuration with a secondary shape. In another feature of the fifth aspect of the invention, the composite cable can further comprise at least one longitudinal sensing element for sensing a parameter, such as an optical imaging element, i.e., where the sensing element can comprises an optical fiber. Alternatively, the sensing element can comprise a thermal imaging element, or an ultrasound imaging element, for example.

In a further aspect of the invention, the form about which the three dimensional shape is wound is formed from metal, ceramic or other heat resistant material and has formed within it the path desired for the micro-cable corresponding to the shape. For example, the form can be of a spherical configuration, with the surface containing channels into which the cable is laid prior to heat treating. The channels can be arranged so that the resultant-shape is kink resistant and relatively easy to withdraw without kinking. The form can also contain passages through which the cable can pass to advantageously form the shape.

After the cable is wound around the form, the form and cable can be heat treated to cause the cable material to adopt the shape of the form as a low energy shape. The cable can then be removed from the form and put into a catheter-introducer prior to use in intravascular therapy.

In another presently preferred embodiment, the invention comprises a device for use in interventional therapy and vascular surgery, adapted to be inserted into a portion of a vasculature, comprising a shape memory coil having an outer coil portion and an inner core portion, the shape memory coil having a collapsed primary coil configuration and an expanded secondary configuration with a three dimensional shape; and a radiopaque strand extending through the core of the shape memory coil to provide a radiopaque marker of the deployed configuration of the device. In one presently preferred embodiment, the shape memory coil comprises a multi-stranded coil having a plurality of flexible strands of a resilient material, and in an alternate preferred embodiment, the shape memory coil comprises a single stranded coil, such as of a nickel titanium alloy, or a shape memory polymer, for example. The radiopaque strand enhances the radiopacity of a multi-stranded coil, as well as a single stranded coil of pure nickel titanium alloy, which will advantageously not fray upon stretching, and is stretch resistant. With such an inner radiopaque strand, the coil can also be made of other materials, such as a shape memory polymer such as polyurethane, for example.

In a presently preferred embodiment, the radiopaque strand comprises a core strand having a plurality of intermittently spaced apart enlarged radiopaque portions that can comprise a radiopaque material selected from the group consisting of platinum and gold, for example. The core strand can comprise a material selected from the group consisting of platinum, gold, a shape memory polymer having a glass transition temperature ($T_g$) below 25° C., a hydrogel, an amorphous gel, and a fiber. In one presently preferred aspect, the enlarged radiopaque portions can comprise a plurality of beads of radiopaque material spaced apart and mounted on a core strand of material, and the beads may comprise a radiopaque material selected from the group consisting of platinum, gold and tungsten. In another presently preferred aspect, one or more of the plurality of beads can optionally be bonded to a segment of the shape memory coil, such as an end bead bonded to an end segment of the shape memory coil, for example.

In another presently preferred aspect, the enlarged radiopaque portions may comprise a plurality of coils intermittently wound about and spaced apart on the core strand, and the core strand can comprise a radiopaque material selected from the group consisting of platinum and gold. The spaced apart coils can comprise a radiopaque material selected from the group consisting of platinum and gold.

In another presently preferred embodiment, a polyhedral occlusive device is provided, adapted to be inserted into a portion of a vasculature for occluding a portion of the vasculature, for use in interventional therapy and vascular surgery. The occlusive device can be formed with multiple coils centrally connected together at their inner ends to a central coil body and radiating outward from the central coil body. When inserted within a vessel at a treatment site, such as within an aneurysm, the radiating coil arms of the occlusive device extend to fill the vessel in three dimensions, allowing the occlusive device to accommodate the shape of the vessel.

In another presently preferred embodiment, the device for use in interventional therapy and vascular surgery includes a micro-cable or coil formed of one or more flexible strands of a resilient material, having a collapsed primary coil configuration and an expanded secondary configuration with a three dimensional shape; and one or more therapeutic fibers woven into the coil to enhance treatment of the site after placement of the device. The coil can also be formed to include one or more radiopaque strands to provide a radiopaque marker of the deployed configuration of the device. The one or more therapeutic fibers can be woven about adjacent or non-adjacent loops of the coil, or can be woven through multiple strands of adjacent loops of the coil. The one or more therapeutic fibers are made of a material that will provide a timed release of a therapeutic agent intended to become active after placement of the device, such as human growth hormone, collagen, a modified polymer with growth factor, genetic material for gene therapy, antigens, or the like. A plurality of therapeutic fibers can be provided so that the different fibers in the coil can provide different therapeutic agents to provide a range of therapies.

These and other aspects and advantages of the invention will become apparent from the following detailed description and the accompanying drawings, which illustrate by way of example the features of the invention.

BRIEF DESCRIPTION OF THE DRAWINGS

FIG. 1 is a perspective of a radiopaque microstrand cable constructed according to the invention.

FIG. 2 is a cross-section at 2-2 of FIG. 1.

FIG. 7 is an illustration of a vasoocclusive coil which has been introduced into an aneurysm preparatory to being deployed within the aneurysm.

FIG. 8 is an illustration of a spherical vasoocclusive coil formed with cable of the invention deployed within an aneurysm.

FIG. 9 is an alternate in a preferred embodiment of the invention including a plurality of radiopaque strands within the cable.

FIG. 10 is an alternate preferred embodiment incorporating a therapeutic member within the radiopaque cable of the invention.

FIG. 11 is an alternate preferred embodiment of the present invention wherein strands of the cable are arranged within an exterior binding consisting of multiple straps about the cable.

FIG. 12 is a perspective view of the embodiment of FIG. 11.

FIG. 13 is an alternative embodiment to the embodiment of FIG. 12 wherein the external binding of the cable represents a sheath wound about the cable.

FIGS. 14a and 14b are perspectives of alternative embodiments of the embodiment of FIG. 13.

FIG. 15 is a cross-section of an alternative embodiment in which a plurality of multi-strand cables are included within an external sheath surrounding the cable.

FIG. 16 is a perspective view of the embodiment of FIG. 14.

FIG. 21 is a schematic diagram of a preferred three dimensional radiating coil configuration of a primary wind polyhedral occlusion device according to the principles of the invention.

FIG. 22 is a schematic diagram of an alternate preferred embodiment of a primary wind polyhedral occlusive device according to the principles of the invention.

FIG. 23 is a perspective view of a mandrel for forming the polyhedral occlusive device of FIG. 22.

FIG. 24 is a schematic diagram of an alternate preferred embodiment of a secondary wind polyhedral occlusive device according to the principles of the invention.

FIG. 25 is a perspective view of another preferred alternate embodiment of a helical vasoocclusive coil according to the principles of the invention, with a therapeutic fiber woven around adjacent loops of the coil.

FIG. 26 is a perspective view of another preferred alternate embodiment of a helical vasoocclusive coil according to the principles of the invention, with a plurality of therapeutic fibers woven around adjacent loops of the coil.

FIG. 27 is a perspective view of another preferred alternate embodiment of a helical multi-stranded vasoocclusive coil according to the principles of the invention, with a therapeutic fiber woven through strands of adjacent loops of a multi-stranded coil.

FIG. 28 is a perspective view of another preferred alternate embodiment of a helical multi-stranded vasoocclusive coil according to the principles of the invention, with a plurality of therapeutic fibers woven through strands of adjacent loops of a multi-stranded coil.

DETAILED DESCRIPTION OF THE PREFERRED EMBODIMENTS

Figure 3:
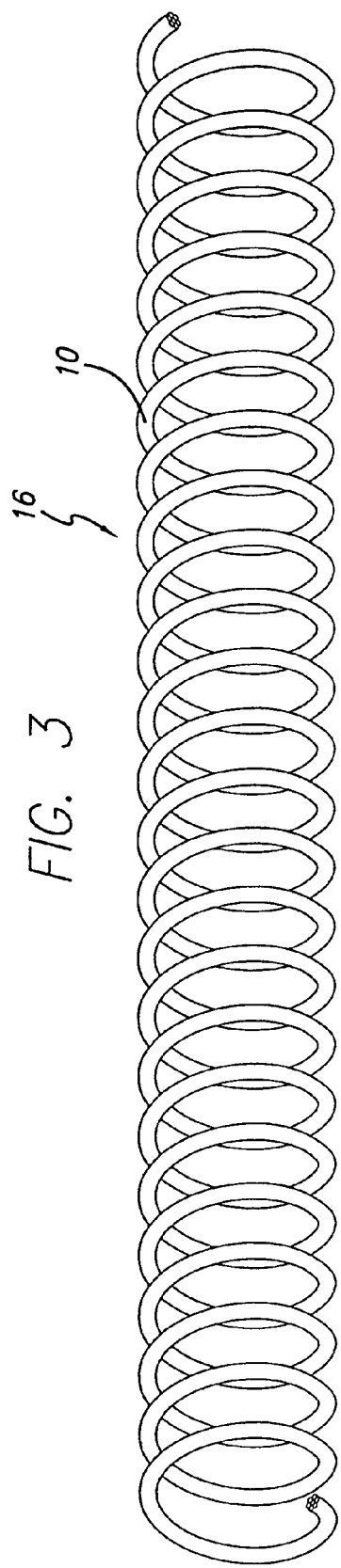
FIG. 3 is a helical vasoocclusive coil formed of the cable of the invention.

While nickel-titanium alloys are useful in forming super-elastic or shape memory interventional devices, micro-coils formed of very small diameter wires of nickel-titanium alloy material for treatment of areas of the small diameter vasculature such as an artery or vein in the brain, for treatment of aneurysms and the like, for example, can have relatively low yield strengths and are somewhat subject to kinking, even if made of super-elastic alloy. This can create problems if the coil is to be withdrawn after being emplaced by the doctor, as for instance, if the device is too small to effectively fill the cavity to be treated. Furthermore, even solid wires of a size suitable for use in interventional devices are not very radiopaque.

As is illustrated in the drawings, which are provided for the purposes of illustration and not by way of limitation, the invention is embodied in a multi-stranded micro-cable formed of a plurality of flexible strands of a resilient material with the cable including at least one radiopaque strand. In a presently preferred embodiment of the invention illustrated in FIG. 1, the multi-stranded micro-cable 10 is approximately from 0.0015 to 0.009 inches in diameter, and comprises a plurality of flexible strands 12 of nickel-titanium alloy, with at least one centrally, axially disposed radiopaque wire 14 which is approximately from 0.0005 to 0.003 inches in diameter. While the above stated diameters represent those presently known to be compatible with the invention, larger or smaller diameters may be useful for particular applications. The central radiopaque wire 14 can be formed of platinum or gold, for example, or other similar suitable radiopaque metals, in order to provide a radiopaque marker of the deployed configuration of a device made of the cable during vascular surgery.

There are numerous benefits to the novel construction of the invention for use in interventional devices and the like. By using the stranded or micro-cable construction of the invention, a device made from the micro-cable becomes virtually kink resistant compared to the single strand wires now commonly used in micro-coils. The multi-strand cable construction of the invention allows the micro-wires of the cable to slip across each other and reinforce each other rather than break or take a set. Also, by incorporating a stranded radiopaque material such as platinum, tungsten or gold into the cable construction, the device is radiopaque in sizes much smaller than with other constructions. The micro-cable construction of the invention can be used to produce soft, kink resistant, radiopaque stents, guidewires, guidewire distal tips, and micro-coils.

FIG. 2 is a cross-section of the micro-cable of FIG. 1 at 2-2 illustrating one presently preferred arrangement of the strands within the cable. In this embodiment, the exterior strands 12 are formed of a resilient material chosen to provide the characteristics desired for a specific application in interventional therapies. In a presently preferred embodiment, this material is a nickel titanium super-elastic alloy which is heat treated such that the alloy is highly flexible at a temperature appropriate for introduction into the body via a catheter. By choosing such a material for micro-coils and the like, the devices formed from the micro-cable can be relatively easily placed into the appropriate body cavity and after placement, the device will take on a shape designed to optimize the therapeutic purposes desired for the device. As illustrated in FIG. 2, such a cable can have a central core 14 of a radiopaque material such as gold or platinum, thus dramatically enhancing the radiopacity of the cable. Even a solid super-elastic wire of the same diameter as the cable would have substantially less radiopacity than the cable of the invention with the central gold or platinum wire and the construction of the invention provides numerous other highly desirable characteristics. Among these characteristics is the relative flexibility and resistance to kinking of the cable compared to an equivalent single wire and substantially greater accommodation of the cable to bending, etc., with resultant lessening of trauma to the surrounding tissue and ease of placement in a small body cavity.

Figure 5:
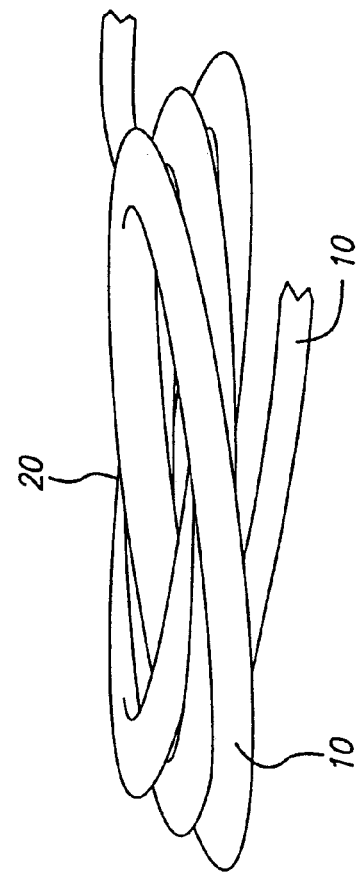
FIG. 5 is a stacked coil vasoocclusive device formed using the cable of the invention.
Figure 4:
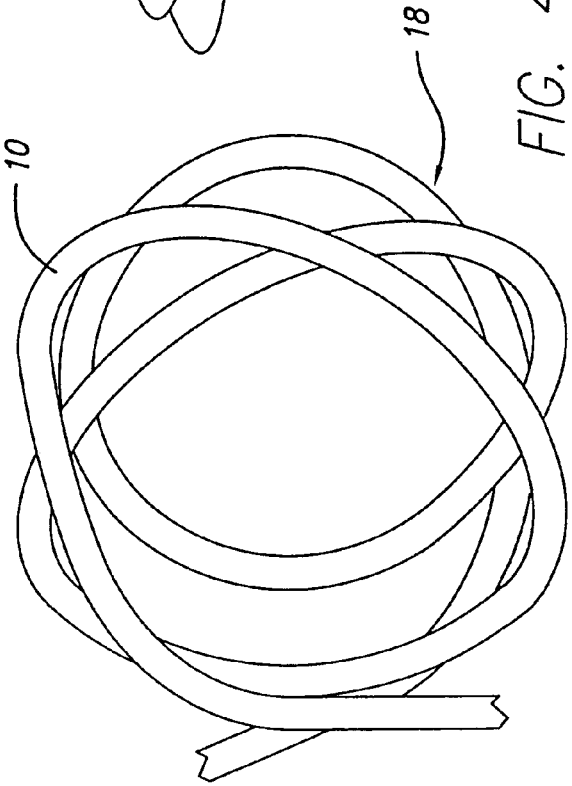
FIG. 4 is a spherical vasoocclusive structure formed using the cable of the invention.

One advantageous application of the invention is to vasoocclusive devices formed of the micro-cable for insertion into aneurysms and other vascular defects for the purpose of occluding flow to the aneurysm. FIG. 3 illustrates a helically wound coil 16 of micro-cable 10 which is formed to fit within a micro-catheter for insertion into an area upon which a therapeutic procedure is to be performed. While a helical coil is illustrated, it will be appreciated that numerous other secondary shapes can be formed from the cable of the invention, as will be described further below. More specifically, as illustrated in FIG. 4, a three dimensional, essentially spherical, device 18 can be formed of the cable 10, (or even of a coil of the cable, if appropriate) at a temperature sufficient to heat treat the material and thereby create a memory of the desired shape. The device is then inserted into a catheter from which it may be deployed into an aneurysm or the like. The teachings of U.S. Pat. No. 5,645,558 describe the construction of such a device out of flexible wire and are incorporated by referenced herein. FIG. 5 illustrates a collapsed coil configuration 20 for a vasoocclusive device which also can be formed from the cable of the invention and is used for the purposes of insertion into aneurysms and other defects that have relatively large entry necks compared to their internal volume.

Figure 6:
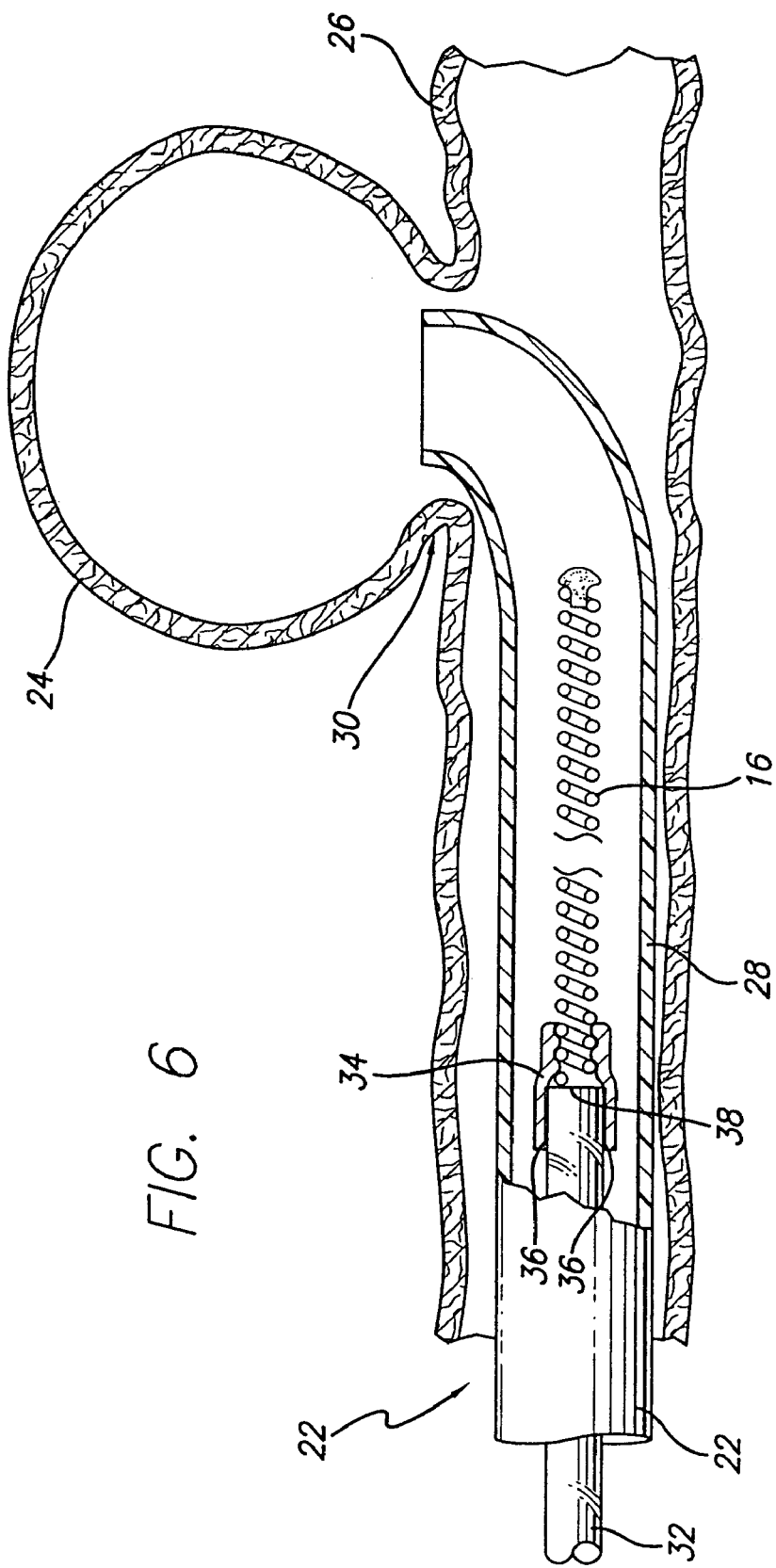
FIG. 6 is a cross section of a vascular member with an aneurysm illustrating the approach of a vasoocclusive coil towards the aneurysm.

FIG. 6 is an illustration of a catheter 22 using a coil 16 as a vasoocclusive device made of the present invention and used for insertion into an aneurysm 24 projecting laterally from a blood vessel 26. The coil 16 is contained within the outer housing 28 of a micro-catheter that is used to house the coil prior to deployment. The end of the catheter housing 28 is introduced into the opening 30 of the aneurism 24 by use of a guide wire (note shown). Thereafter, the vasoocclusive coil 16, and a pusher 32 are introduced into the catheter to provide for insertion of the vasoocclusive device into the aneurysm. In a presently preferred embodiment, the coil 16 formed of the cable of the invention is retained to an optical fiber pusher 32 which is attached to the coil by a collar of shape memory plastic material 34 as described in co-pending application Ser. No. 08/986,004 the disclosure of which are incorporated herein by reference. As shown in FIG. 7, the coil is introduced into the aneurysm and is then pushed from the micro-catheter until it fills the cavity.

Those skilled in the art will recognize that it is sometimes the case that the vasoocclusive device must be withdrawn after it is fully or partly inserted into the aneurysm. In such a case, there is a danger that the coil will be stretched beyond its elastic range or kink, or otherwise deform and make withdrawal difficult. Those skilled in the art will also recognize that it is sometimes advantageous to form vasoocclusive devices of secondary shapes which are based upon a basic configuration of a coil or the like. The present invention includes such applications within the scope of the invention. However, when vasoocclusive devices made of even super-elastic material are used, it is sometimes the case that the devices will be stretched or kinked when withdrawal is attempted. The cable of the present invention substantially reduces the probability that kinking or stretching beyond yield will occur in a given instance, while at the same time providing radiopacity not available with other constructions. Thus, the present invention represents an important forward step in the technology of interventional therapy.

In one presently preferred embodiment, the shape memory collar 34 is heated to a temperature which allows it to be shrunk onto coil 16. The collar is attached to optical fiber pusher 32 by an adhesive 36 which retains high strength at temperatures beyond the shape memory material transition point. After insertion, and when the operator is satisfied that the device is properly deployed, light energy from a source of coherent light is introduced into the proximal end of the optical fiber (not shown) and propagated in the distal end 38 of the fiber to cause the shape memory material collar 34 to return to its previous shape and release coil 16. Those skilled in the art will recognize that the invention can also be used with a variety of other placement catheter systems, and it is not intended that the invention be limited to the placement concepts illustrated by way of example.

Those skilled in the art will recognize that a number of shaped devices may be introduced into an area to be treated depending upon its geometry and the number of devices to be inserted. FIG. 8 illustrates an essentially spherical device 18 which has been deployed into such an aneurysm but it will commonly be found that a device such as that shown would then be supplemented by a further coiled device inserted within the space inside the spherical device to completely occlude flow from the artery to the aneurysm.

While one presently preferred implementation of the micro-cable of the invention has been illustrated, those skilled in the art will appreciate that other variations of the invention may have advantages for certain purposes. FIG. 9 is an example of one such construction 40 in which radiopacity is more desirable than in other forms and for that reason a number of radiopaque strands 42, in this illustration four in number, are formed into the cable along with three resilient material strands 44. It will also be appreciated that a larger or smaller number of strands may be incorporated into a given cable and the cables may be formed of multiple cables in order to provide desired bending and strength characteristics. It will also be appreciated by those skilled in the art that the invention is adaptable to the use of a variety of materials which by themselves would not have been easily adaptable to micro devices for interventional therapies. For instance, materials such as copper are useful for intrauterine devices and the like, but copper wire, even when heavily alloyed, has certain limitations for use in such devices. By use of the present invention, composite cables incorporating one or more strands of a desired material can be configured with other strands providing strength, flexibility, shape memory, super-elasticity, radiopacity or the like for previously unavailable characteristics in micro devices.

The invention is also adaptable to numerous other purposes. FIG. 10 illustrates a cross-section of a further preferred embodiment in which radiopaque strands 42 and resilient strands 44 form a portion of the cable and a therapeutic agent 48 is contained in one of the strands. Such a therapeutic agent can include human growth hormone, hydrogels, or a variety of other agents which will serve to provide desired therapeutic capabilities when placed within a specific area of the body being treated by use of the micro-catheter. Depending upon the application of the therapeutic agent, its method of action and the delay, if any, in the time after placement in which the therapeutic action is desired, the agent strand may be placed in any of a variety of positions with the cable, from core wire outward. Also, it may be desirable to coat one or more strands with a therapeutic material for certain purposes. Such constructions are contemplated within the scope of the invention.

It is also contemplated within the scope of the invention that one or more of the strands of the micro-cable is longer than the others, and perhaps intermittently terminated, to thereby produce a micro-cable in which the therapeutic strands extend to a greater diameter than the other strands to thus increase the therapeutic effect of the therapeutic stand. Such a construction is particularly advantageous if increased thrombogenicity is desired, while maintaining structural continuity and radiopacity for the micro-cable.

FIG. 11 illustrates a cross-section of an additional presently preferred embodiment of the invention in which the strands 12, 14 of the micro-cable 10 are bundled and banded at intervals by bands 50 to produce a composite banded cable 52 in order to provide increased flexibility without unraveling or dislocation of the strands in the cable. FIG. 12 is a perspective view of the banded cable 50 of this embodiment. While the illustrated configuration shows the strands being laid parallel within the cable, it is also possible in this construction to include both twisted cables as the primary cables 10 within the outer bands 50 to form the composite cable 52. This configuration can use one or more longitudinal strands 14 which are radiopaque, thus providing a continuous indication of radiopacity within the cable. As a further alternative embodiment, it is possible for the longitudinal cable 52 to be formed of a single inner cable 10 with bands 50.

FIG. 13 illustrates a further embodiment of the invention in which longitudinal strands of cables are contained within a wound cover 56 for the purposes of providing a composite guide wire or the like 58 having improved torqueability. Such a construction has particular advantages for guidewire designs having improved radiopacity in very small diameters. It will be appreciated that in this configuration, as well as the other longitudinally arranged multi-stranded cables, the number of strands and the degree to which they extend along the cable within the sheath is a variable which can be used to provide increased stiffness, pushability and torqueability in some sections with greater flexibility in others. Additionally, composite cables according to the invention can incorporate additional elements normally not available in solid guide wires, such as optical, thermal or ultrasound imaging elements, therapeutic agent delivery catheters, and can take advantage of materials which are not readily adaptable to prior art catheter or guide wire designs incorporating a primary wire structured element. FIGS. 14a and 14b illustrate a further variable available because of the invention; the exterior wrapped cover 56 can be wound at greater or lesser intervals 60 along the outside to provide variations in the torqueability and stiffness of the composite cable. Also, the thickness and width of the wrapping cover 56, as well as its material composition along the composite guide wire 58, can offer further capabilities for customizing the design for various applications. These advantages can be combined with the benefits of shape memory or super-elastic alloys to create guidewires and other devices with heretofore unavailable capabilities.

FIG. 15 illustrates a cross-section of a micro-cable according to the invention which has at least one overall exterior sheath to contain the micro-cable. The micro-cable may be made of one or more multiple strand elements which may further include twisted or longitudinal strands within their construction. The sheath may also be used to control the torqueability characteristics of the cable and as discussed in co-pending application Ser. No. 08/986,004, the sheath may be multi-layered with different materials in order to provide a graduated bending and stiffness characteristic over the length of the cable.

Referring to FIGS. 17 to 20, in another presently preferred embodiment, a nickel titanium alloy coil, such as the multi-stranded micro-cable described above, can be made radiopaque by the insertion of a radiopaque strand having spaced apart enlarged radiopaque portions into the core of a primary and/or secondary wind. The radiopaque material preferably has a desired degree of stiffness so as not to compromise the desired degree of softness of the coil. The material may comprise a beaded core of platinum, gold, shape memory polymer having a glass transition temperature ($T_g$) below 25° C., polymer, hydrogel, and the like, or a flexible strand, rod, amorphous gel, fiber, and the like. The radiopaque strand can be used to enhance the radiopacity of the multi-stranded coil, as indicated above, as well as a pure nickel titanium alloy coil, which will advantageously not fray upon stretching, and is stretch resistant. With such an inner radiopaque strand, the coil can also be made of other materials, such as a polyurethane shape memory polymer, for example.

Figure 17:
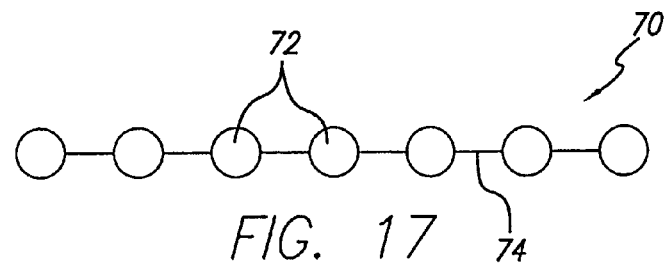
FIG. 17 is a plan view of a beaded radiopaque strand according to another preferred embodiment of the invention.
Figure 18:
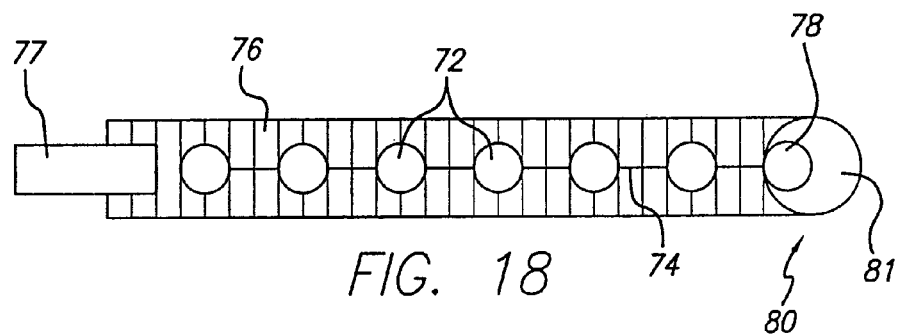
FIG. 18 is a sectional view of the beaded radiopaque strand of FIG. 17 inserted in a shape memory coil.

In a presently preferred embodiment illustrated in FIGS. 17 and 18, the radiopaque strand 70 may comprise a plurality of beads 72 of radiopaque material, such as platinum, gold or tungsten, spaced apart and mounted, such as by soldering, welding, or adhesive bonding such as by cyanoacrylate adhesive, on a core strand 74 of material that can be platinum, gold or tungsten, or a shape memory polymer having a glass transition temperature ($T_g$) below 25° C. The beaded radiopaque strand can form the central core of a multi-stranded micro-cable, and as is shown in FIG. 18, the beaded radiopaque strand 70 may form a core of a pure nickel titanium alloy coil 76 wound around the beaded radiopaque strand, and having a proximal stem 77 bonded to the coil by soldering, welding, adhesive or the like, that can also be formed as a radiopaque marker, of such materials as platinum, gold or tungsten, for example. In a preferred aspect, one or more beads, such as an end bead 78, may optionally be bonded to a segment 80 of the coil, such as by cyanoacrylate adhesive 81, for example.

Figure 19:
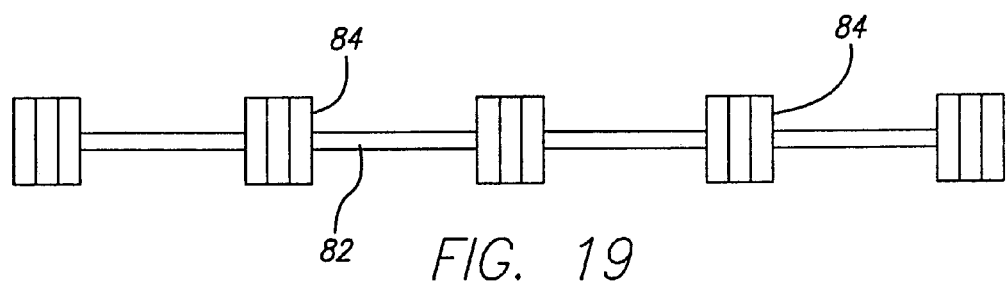
FIG. 19 is a plan view of an alternate preferred embodiment of a radiopaque strand with intermittent spaced apart coils.

In another presently preferred embodiment illustrated in FIG. 19, the radiopaque strand can comprise a radiopaque wire 82, such as platinum or gold, for example, intermittently wound with a plurality of spaced apart coils 84 of radiopaque material, such as platinum or gold, for example, to form an inner radiopaque core for a multi-stranded micro-cable, or in an alternate preferred embodiment, the intermittently wound radiopaque strand may form a core of a pure nickel titanium alloy coil wound around the intermittently wound radiopaque strand.

Figure 20:
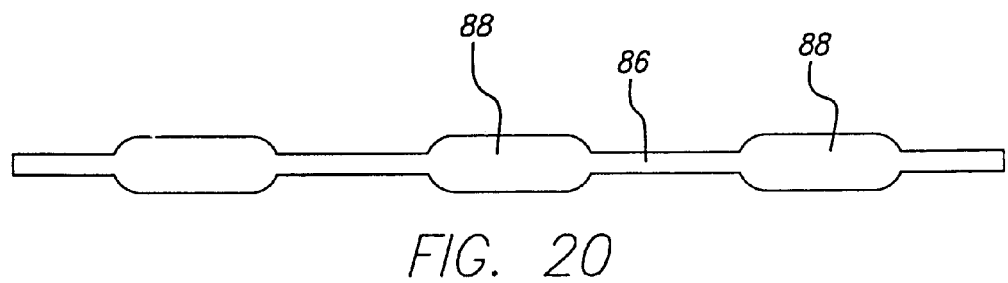
FIG. 20 is a plan view of an alternate preferred embodiment of the radiopaque strand having spaced apart enlarged radiopaque portions.

Referring to FIG. 20, in another presently preferred embodiment, the radiopaque strand can comprise a radiopaque wire 86, such as platinum or gold, for example, with intermittently spaced apart enlarged radiopaque portions 88, to form an inner radiopaque core for a multi-stranded micro-cable, or for a pure nickel titanium alloy coil wound around the radiopaque strand.

It will be appreciated that a three dimensional occlusive device adapted to be inserted into a portion of a vasculature for occluding the portion of the vasculature for use in interventional therapy and vascular surgery, can be formed as described above, from at least one multi-stranded micro-cable having a plurality of flexible strands of a resilient material, with at least one radiopaque strand to provide a radiopaque marker for the device during vascular surgery. The occlusive device is configured to have a primary coil shape, as illustrated in FIG. 5, and an expanded secondary three dimensional coil configuration or shape, that can be generally helical, conical, or spherical shapes, such as the spherical shapes illustrated in FIGS. 4 and 8. A mandrel suitable for making such three dimensionally shaped occlusive devices can be formed of a refractory material, such as alumina or zirconia, for example. The mandrel typically has the general three dimensional shape that the occlusive device will be given, and can have a generally helical, conical, or spherical shape, or can have a unique shape designed to provide such a form to the occlusive device to fit a particular vascular structure to be treated. The mandrel forms a support for the winding and heat treatment of the micro-cable, plurality of microcables, or composite micro-cable occlusive device as described above, and ideally will not contaminate the occlusive device during heat treatment of the device. The surface of the mandrel preferably has a plurality of circumferential grooves for aligning the occlusive device as it is wound on the mandrel. The surface of the mandrel may also have one or more apertures for receiving one or more ends of the micro-cable, plurality of micro-cables, or composite micro-cable, to assist winding into the desired form.

The wound occlusive device is then heat treated at a suitable temperature and a sufficient period of time to impart the form to the shape memory material included in the device. While heat treatment at a temperature of about 1100° F. for approximately 4 hours or more is typically sufficient to impart the form to the occlusive device when the shape memory material is a nickel titanium super-elastic alloy, but when the occlusive device includes fibers or a therapeutic agent that can be affected by heat, the temperature utilized can be substantially lowered, and the duration of heat treatment adjusted accordingly, as will be appreciated by those skilled in the art. Alternatively, if the therapeutic agent is not amenable to elevated temperatures, it may be added after formation of the three dimensional shape. After the heat treatment, the occlusive device is removed from the mandrel, and cold worked into the desired collapsed primary configuration for placement into a catheter or cannula for use. It will be appreciated that those techniques can also be used for a variety of cables produced according to the invention, including those which use shape memory materials other than nickel-titanium alloys. When the occlusive device reaches its destination in the vasculature during vascular therapy, it assumes the secondary relaxed and expanded three dimensional shape imparted from the heat treatment on the mandrel.

In another presently preferred embodiment, a three dimensional, polyhedral occlusive device is provided, adapted to be inserted into a portion of a vasculature for occluding a portion of the vasculature, for use in interventional therapy and vascular surgery. The occlusive device can be formed as described above, from at least one multi-stranded micro-cable having a plurality of flexible strands of a resilient material, with at least one radiopaque strand to provide a radiopaque marker for the device during vascular surgery, with multiple coils, preferably four or more coils, centrally connected together at their inner ends, and in a presently preferred aspect, connected at their inner ends to a central coil body and radiating outward from the central coil body. When inserted with a vessel at a treatment site, such as within an aneurysm, the radiating coil arms of the occlusive device extend to fill the vessel in three dimensions, allowing the occlusive device to accommodate the shape of the vessel. In a preferred aspect, the radiating coils of the occlusive device can thus form a tetrahedral, pentahedral, hexahedral, or other polyhedral shape, symmetrical or unsymmetrical, and are preferably formed from conically shaped coil arms that have an expanding diameter as they radiate outward from the central coil body, with the radiating coil arms having soft larger diameter outer ends. The central coil body may be spherical or rounded, or may be correspondingly cubical, tetrahedral, pentahedral, or otherwise appropriately polyhedral. A typical aneurysm may have a diameter of approximately 10 mm., and the coil arms will also typically have an outer diameter of approximately 10 mm.

As is illustrated in FIG. 21, one presently preferred three dimensional radiating coil configuration 90 is a primary wind coil having a hexahedral configuration with six conically shaped coil arms 92 radiating from a central coil junction 94 in the three x, y and z axes of a three dimensional pattern of coordinates. Such a three dimensional radiating coil configuration can be formed by individually winding the radiating arms of the hexahedral configuration on conically shaped mandrel, and bonding the inner apical ends 96 of the coils together by welding, solder, adhesive such as cyanoacrylate, or the like. A central coil body 98 such as the spherical coil described above is also preferably similarly bonded to the inner ends of the coil arms.

Referring to FIG. 22, in another presently preferred embodiment, a three dimensional radiating hexahedral coil configuration 100 for the occlusive device is also a primary wind coil with six conically shaped coils or coil arms 102 radiating from a central coil ball or sphere 104 in the three x, y and z axes forming a three dimensional pattern of coordinates. The central ball may also alternatively have the shape of a cube, for example. The outer diameter of the coil arms typically can be approximately 10 mm., and the diameter of the central coil ball or sphere typically can be 3 mm. in diameter. The hexahedral coil can be formed by winding the central spherical coil about a mandrel as described above and then joining the six radiating conical coil arms at their inner apical ends 106 to the central spherical coil 108, as described above, such as by welding, solder, adhesive such as cyanoacrylate, or the like. Alternatively, the hexahedral coil configuration can be formed as a continuous primary wind of the coil by winding the central spherical coil, and forming the radiating arms by a double winding of the radiating conical coil arms, first up from the center and then back down, with each of the radiating conical coil arms being wound in turn about the central spherical at the appropriate location.

Referring to FIG. 23, such a hexahedral configuration with six conically shaped coils radiating from a common central coil ball or sphere can be formed by winding the coils about a mandrel 110 formed of a refractory material, such as alumina or zirconia, for example, and having inverted conical coil arms 112 radiating from a central body 114, such as a spherical, rounded, cubical, tetrahedral, pentahedral, or otherwise polyhedral central body, for example. The mandrel forms a support for the winding and heat treatment of the three dimensional radiating hexahedral coil occlusive device as described above, and ideally will not contaminate the occlusive device during heat treatment of the device. The surface of the central body of the mandrel preferably has a plurality of circumferential grooves 116 for aligning the occlusive device as it is wound on the mandrel. The surface of the mandrel may also have one or more apertures 118 for receiving one or more ends of the micro-cable, plurality of microcables, or composite micro-cable forming the hexahedral occlusive device, to assist winding into the desired form.

In another configuration illustrated in FIG. 24, a another presently preferred alternate three dimensional radiating coil configuration 120 is a secondary wind coil of a primary wind coil, such as a helical wind, for example, the secondary wind coil having a hexahedral configuration with six conically shaped coil arms 122 radiating from the common central coil 124, which is illustrated as having a cubical shape, in the three x, y and z axes of a three dimensional pattern of coordinates. The outer diameter of the coil arms typically can be approximately 10 mm., and the diameter of the central coil ball or sphere typically can be 3 mm. in diameter. The hexahedral secondary wind configuration can be formed by winding the primary helical wind coil about an appropriate mandrel, and then joining the six radiating conical coil arms at their inner apical ends 126 to the common central coil 128, as described above, such as by welding, solder, adhesive such as cyanoacrylate, or the like. Alternatively, the hexahedral coil configuration can be formed as a continuous primary wind of the coil by winding the central coil body, and forming the radiating arms by a double winding of the radiating conical coil arms, first up from the center and then back down, with each of the radiating conical coil arms being wound in turn about the central spherical at the appropriate location.

As is described above, the tetrahedral, pentahedral, hexahedral or other polyhedral wound occlusive device radiating from the common central coil is then preferably heat treated upon the mandrel at a suitable temperature and for a sufficient period of time to impart the relaxed form to the shape memory material forming the device. The occlusive device can then be cold worked into a shape suitable for delivery through a catheter to a desired treatment site, and when the occlusive device reaches its destination in the vasculature during vascular therapy, it assumes the relaxed and expanded three dimensional shape imparted from the heat treatment on the mandrel.

In another presently preferred embodiment illustrated in FIGS. 25 and 26, a helical microcoil 130 that can be formed of one or more flexible strands of nickel-titanium alloy, has one or more therapeutic fibers 136 advantageously woven about adjacent loops of the coil, used to enhance treatment of the site after placement of the device. The helical microcoil can also be formed to include one or more axially disposed radiopaque wires, as described above. Alternatively, the one or more therapeutic fibers can be woven about non-adjacent loops of the coil as well. The therapeutic fibers are preferably made of a material that will provide a timed release of a therapeutic agent, such as human growth hormone, collagen, a modified polymer with growth factor, genetic material for gene therapy, antigens or the like, that are intended to become active after placement. When multiple fibers are provided, as is shown in FIG. 26, different fibers can be provided in the same coil with different therapeutic agents to provide different therapies. The fibers are preferably woven into the coil by hand after the heat setting of the coil shape.

In another presently preferred embodiment illustrated in FIGS. 27 and 28, a helical microcoil 140 formed of a plurality of flexible strands 142 of nickel-titanium alloy, with at least one centrally, axially disposed radiopaque wire 144 as described above, has one or more therapeutic fibers 136 as described above, advantageously woven through the multiple strands of adjacent loops of the coil, to enhance treatment of the site after placement of the device. Alternatively, the one or more therapeutic fibers can be woven through the strands of non-adjacent loops of the coil as well. When multiple fibers are provided, as is shown in FIG. 28, the different fibers can be provided in the same coil with different therapeutic agents to provide different therapies. The one or more fibers are preferably woven through the strands of the multiply-stranded microcoil by hand during winding of the multiply-stranded microcoil.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An occlusive device for use in interventional therapy and vascular surgery, adapted to be inserted into a portion of a vasculature, said occlusive device comprising:
    a central coil body; and
    at least four coil arms formed of shape memory material having a collapsed primary coil configuration and a three dimensional, expanded secondary configuration, wherein said at least four coil arms are formed from conically shaped coils each having an inner apical end and an outer end, said inner apical ends being connected together and to said central body, and said conically shaped coils having an expanding diameter as they radiate outward.

2. The occlusive device of claim 1, wherein said central body comprises a central three dimensional coil connecting said inner apical ends of said at least four coil arms together and said central three dimensional coil has a shape selected from the group consisting of spherical, rounded, and cubical shapes.

3. The occlusive device of claim 1, wherein said at least four coil arms comprise at least one multi-stranded microcable having a plurality of flexible strands of a resilient material, with at least one radiopaque strand to provide a radiopaque marker.

4. The occlusive device of claim 1, wherein said at least four coil arms comprise at least one secondary wind coil of a primary helical wind coil.

5. An occlusive device for use in interventional therapy and vascular surgery, adapted to be inserted into a portion of a vasculature, said occlusive device comprising:
    a central coil body;
    at least four coil arms formed of shape memory material having a collapsed primary coil configuration and a three dimensional, expanded secondary configuration, wherein said at least four coil arms are formed from conically shaped coils each having an inner apical end and an outer end, said inner apical ends being connected together and to said central body, and said conically shaped coils having an expanding diameter as they radiate outward; and
    wherein said central body comprises a central three dimensional coil connecting said inner apical ends of said at least four coil arms together and said central three dimensional coil comprises a secondary wind coil of a primary helical wind coil.

6. A device for use in interventional therapy and vascular surgery, adapted to be inserted into a portion of a vasculature, comprising:
    a shape memory coil having an outer coil portion and an inner core portion, said shape memory coil having a primary, collapsed coil configuration and a secondary, expanded configuration with a three dimensional shape; and
    a radiopaque strand having a plurality of intermittently spaced apart enlarged portions disposed within the outer coil portion.

7. The device of claim 6, wherein said shape memory coil comprises a multi-stranded coil having a plurality of flexible strands of a resilient material.

8. The device of claim 7, wherein at least one of said flexible core strands comprises a radiopaque material selected from the group consisting of platinum and gold.

9. The device of claim 7, wherein at least one of said flexible core strands comprise a material selected from the group consisting of platinum, gold, a shape memory polymer having a glass transition temperature (Tg) below 25° C., a hydrogel, an amorphous gel, and a fiber.

10. The device of claim 6, wherein said shape memory coil comprises a single stranded coil.

11. The device of claim 10, wherein said single stranded coil comprises a nickel titanium alloy.

12. The device of claim 10, wherein said single stranded coil comprises a shape memory polymer.

13. The device of claim 6, wherein said enlarged portions comprise a radiopaque material selected from the group consisting of platinum and gold.

14. The device of claim 6, wherein said enlarged portions comprise a plurality of beads of radiopaque material spaced apart and mounted on a core strand of material.

15. The device of claim 14, wherein said beads comprise a radiopaque material selected from the group consisting of platinum, gold and tungsten.

16. The device of claim 14, wherein at least one of said plurality of beads is bonded to a segment of the shape memory coil.

17. The device of claim 14, wherein said enlarged portions comprise a plurality of coils intermittently wound about and spaced apart on said core strand.

18. The device of claim 17, wherein said spaced apart coils comprise a radiopaque material selected from the group consisting of platinum and gold.

* * * * *

UNITED STATES PATENT AND TRADEMARK OFFICE
CERTIFICATE OF CORRECTION

| | | |
|---|---|---|
| PATENT NO. | : 7,326,225 B2 | Page 1 of 1 |
| APPLICATION NO. | : 10/628767 | |
| DATED | : February 5, 2008 | |
| INVENTOR(S) | : Ferrera et al. | |

It is certified that error appears in the above-identified patent and that said Letters Patent is hereby corrected as shown below:

On the Title page, Item (63) Related U.S. Application Data, delete "Continuation of application No. 09/762,539, filed as application No. PCT/US98/25822 on Dec. 4, 1998, now Pat. No. 6,616,617" and insert --Continuation of application No. 09/762,539 filed Feb. 8, 2001, now U.S. Pat. No. 6,616,617, which is a 371 of International PCT/US98/25822 filed Dec. 4, 1998,--

On the Title Page Item (56) Other Publications, page 3, delete "Investigate" in the reference Stephen L. Kaufman, M.D. and insert instead --Investigative--.

Column 5, lines 41-44, delete "Such a construction can be adapted to a variety of interventional therapeutic treatments, such as providing both a therapeutic effect and also contributing to the structural integrity of the cable." and insert --The core of the cable contains a therapeutic agent such as human growth hormone, genetic material, antigens or the like that are intended to become active after placement. Such a construction can be adapted to a variety of interventional therapeutic treatments. In one aspect of this embodiment, one of the strands can have multiple functions, such as providing both a therapeutic effect and also contributing to the structural integrity of the cable.--

Signed and Sealed this
Fifteenth Day of February, 2011

David J. Kappos
*Director of the United States Patent and Trademark Office*